United States Patent
Nishiura et al.

(10) Patent No.: US 9,349,968 B2
(45) Date of Patent: May 24, 2016

(54) ORGANIC METAL COMPLEX AND ORGANIC ELECTROLUMINESCENCE DEVICE USING THE COMPLEX

(75) Inventors: Chiaki Nishiura, Kawasaki (JP); Takayuki Horiuchi, Tokyo (JP); Hiroya Nitta, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 407 days.

(21) Appl. No.: 14/122,067

(22) PCT Filed: Jul. 27, 2012

(86) PCT No.: PCT/JP2012/069781
§ 371 (c)(1),
(2), (4) Date: Nov. 25, 2013

(87) PCT Pub. No.: WO2013/018876
PCT Pub. Date: Feb. 7, 2013

(65) Prior Publication Data
US 2014/0146247 A1  May 29, 2014

(30) Foreign Application Priority Data

Aug. 2, 2011 (JP) ................................. 2011-168943

(51) Int. Cl.
*H01L 51/54* (2006.01)
*C09K 11/06* (2006.01)
*H01L 51/00* (2006.01)
*C07D 405/04* (2006.01)
*C07F 15/00* (2006.01)
*H05B 33/14* (2006.01)
*H01L 27/32* (2006.01)
*H01L 51/50* (2006.01)

(52) U.S. Cl.
CPC .......... *H01L 51/0085* (2013.01); *C07D 405/04* (2013.01); *C07F 15/0033* (2013.01); *C07F 15/0086* (2013.01); *C09K 11/06* (2013.01); *H01L 27/323* (2013.01); *H01L 51/0087* (2013.01); *H05B 33/14* (2013.01); *C09K 2211/1014* (2013.01); *C09K 2211/1029* (2013.01); *C09K 2211/1088* (2013.01); *C09K 2211/185* (2013.01); *H01L 51/0059* (2013.01); *H01L 51/0067* (2013.01); *H01L 51/0072* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,976,958 B2 | 7/2011 | Takiguchi et al. |
| 8,268,455 B2 | 9/2012 | Kamatani et al. |
| 2007/0231600 A1 | 10/2007 | Kamatani et al. |
| 2008/0131730 A1 | 6/2008 | Takiguchi et al. |

FOREIGN PATENT DOCUMENTS

| | | |
|---|---|---|
| JP | 2007-269734 A | 10/2007 |
| JP | 2008-133212 A | 6/2008 |
| WO | 2006/114966 A1 | 11/2006 |
| WO | 2011/136156 A1 | 11/2011 |

OTHER PUBLICATIONS

King et al., "Excited-State Properties of a Triply Ortho-Metalated Iridium(III) Complex," J. Am. Chem. Soc., vol. 107, pp. 1431-1432 (1985).

Dedeian et al., "A New Synthetic Route to the Preparation of a Series of Strong Photoreducing Agents: fac Tris-Ortho-Metalated Complexes of Iridium(III) with Substituted 2-Phenylpyridines," Inorg. Chem., vol. 30, pp. 1685-1687 (1991).

Aoki et al., "Regioselective Aromatic Substitution Reactions of Cyclometalated Ir(III) Complexes: Synthesis and Photochemical Properties of Substituted Ir(III) Complexes That Exhibit Blue, Green, and Red Color Luminescence Emission," Inorg. Chem., vol. 50, pp. 806-818 (2011).

*Primary Examiner* — Marie R. Yamnitzky
(74) *Attorney, Agent, or Firm* — Fitzpatrick, Cella, Harper & Scinto

(57) ABSTRACT

To provide an organic electroluminescence device that emits blue light and is excellent in luminescence properties (in particular, external quantum yield), and provide an organic metal complex including xanthone in a ligand of the following formula (1).

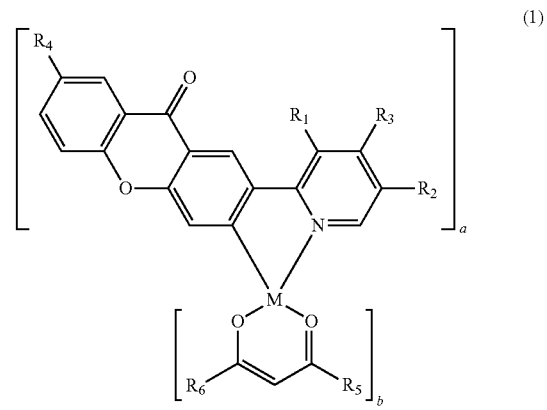

8 Claims, 1 Drawing Sheet

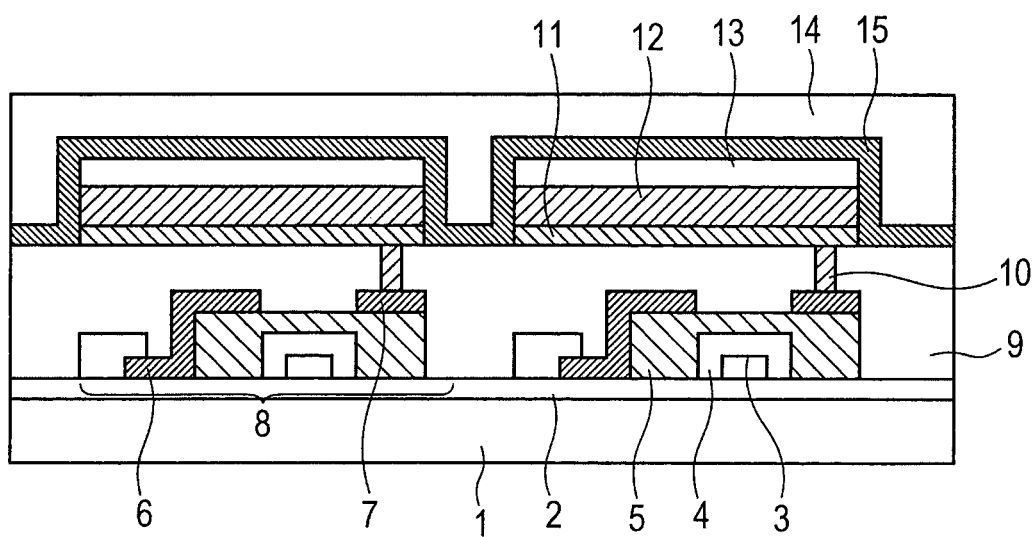

ORGANIC METAL COMPLEX AND ORGANIC ELECTROLUMINESCENCE DEVICE USING THE COMPLEX

TECHNICAL FIELD

The present invention relates to an organic metal complex and an organic electroluminescence device using the complex.

BACKGROUND ART

An organic electroluminescence device (organic EL device) is an electronic element including an anode, a cathode, and an organic compound layer disposed between the anode and the cathode. When electrons and holes are each injected from the respective electrodes (the anode and the cathode), excitons of a light emitting organic compound are produced in the organic compound layer. When the excitons return to the ground state, the organic electroluminescence device emits light.

Recent advances in the organic electroluminescence device are remarkable to provide the following features, for example. That is, the organic electroluminescence device achieves a high luminance at a low driving voltage, has a variety of emission wavelengths and high-speed responsiveness, and allows a light emitting device to be reduced in thickness and weight.

In addition, the creation of a novel light emitting organic compound serving as a constituent material for the organic electroluminescence device has been vigorously performed so far. This is because in providing a high-performance organic electroluminescence device, the creation of a compound for eliciting the performance is important.

In particular, a light emitting material utilizing luminescence from a triplet excited state (phosphorescence) has been vigorously developed because its luminous efficiency can be made high as compared with that of a light emitting material utilizing luminescence from a singlet excited state (fluorescence). At present, however, the material requires an optical output with additionally high luminance or high conversion efficiency. In addition, the material still involves a large number of problems in terms of durability against, for example, a change over time due to long-term use or a reduction in performance due to an atmospheric gas containing oxygen, moisture, or the like. Further, when it is assumed that the material is applied to a full-color display or the like, the material needs to emit blue, green, or red light having a good color purity. However, it cannot still be considered that a problem concerning the need has been sufficiently solved. It can be said that in particular, a blue phosphorescent light emitting material has plenty of room for improvement from the viewpoints of an improvement in color purity and the stability of the material.

The following compounds Z01 (see NPL 1) and Z02 (see NPL 2) have been proposed as examples of an organic compound that emits phosphorescence.

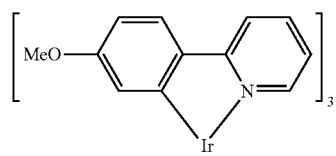

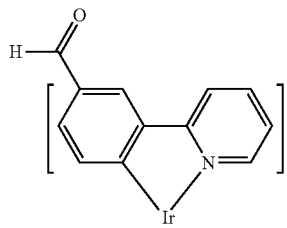

Here, the compound Z01 and the compound Z02 have the following feature in common. Each of the compounds has a ligand using 2-phenylpyridine as a basic structure. It should be noted that the compound Z01 has a methoxy group as an electron-donating group at the 4-position of the phenyl group. Meanwhile, the compound Z02 has a carbonyl group as an electron-withdrawing group at the 5-position of the phenyl group.

CITATION LIST

Non Patent Literature

NPL 1: Inorg. Chem. 1991, 30, 1685-1687
NPL 2: Inorg. Chem. 2011, 50, 806-818
NPL 3: J. Am. Chem. Soc., 1985, 107, 1431

However, the peak wavelengths (emission wavelengths) of the emission spectra of the compound Z01 and the compound Z02 are 481 nm and 477 nm, respectively, and the luminescent color of each of the compounds is bluish green. Therefore, the inventors of the present invention have considered that a material having an additionally short wavelength needs to be searched for in order that blue luminescence having a good color purity can be achieved.

The present invention has been made to solve the problems, and an object of the present invention is to provide an organic electroluminescence device that emits blue light and is excellent in luminescence properties (in particular, external quantum yield).

SUMMARY OF INVENTION

An organic metal complex of the present invention is represented by the following general formula (1).

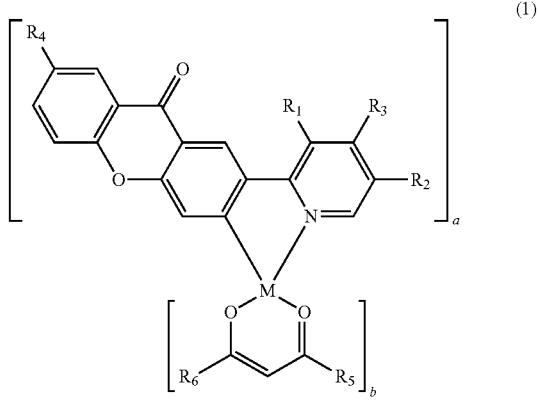

In the formula (1), $R_1$ and $R_2$ each represent a hydrogen atom or an alkyl group having 1 to 4 carbon atoms, $R_3$ represents a hydrogen atom, an alkyl group having 1 to 4 carbon atoms, an alkoxy group having 1 to 6 carbon atoms, or an aryloxy group, $R_4$ represents a hydrogen atom or an alkyl group having 1 to 4 carbon atoms, $R_5$ and $R_6$ each represent an alkyl group having 1 to 4 carbon atoms, M represents Ir or Pt, and a and b each represent an integer, provided that: when M represents Ir, the following requirements (A1) and (A2) are satisfied for a and b: (A1) a+b=3; and (A2) a represents 2 or 3; and when M represents Pt, the following requirements (B1) and (B2) are satisfied for a and b: (B1) a+b=2; and (B2) a represents 1 or 2.

BRIEF DESCRIPTION OF DRAWING

FIGURE is a schematic sectional view illustrating an example of a display device having an organic electroluminescence device of the present invention and a TFT element as an example of a switching element electrically connected to the organic electroluminescence device.

DESCRIPTION OF EMBODIMENTS

First, an organic metal complex of the present invention is described. The organic metal complex of the present invention is a compound represented by the following general formula (1).

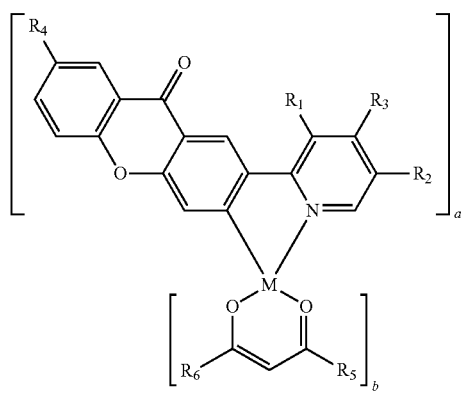

(1)

In the formula (1), $R_1$ and $R_2$ each represent a hydrogen atom or an alkyl group having 1 to 4 carbon atoms.

Examples of the alkyl group represented by each of $R_1$ and $R_2$ include a methyl group, an ethyl group, an n-propyl group, an isopropyl group, an n-butyl group, and a tert-butyl group. In this regard, however, it should be appreciated that the present invention is not limited thereto.

In the formula (1), $R_3$ represents a hydrogen atom, an alkyl group having 1 to 4 carbon atoms, an alkoxy group having 1 to 6 carbon atoms, or an aryloxy group.

Examples of the alkyl group represented by $R_3$ include a methyl group, an ethyl group, an n-propyl group, an isopropyl group, an n-butyl group, and a tert-butyl group. In this regard, however, it should be appreciated that the present invention is not limited thereto.

Examples of the alkoxy group represented by $R_3$ include a methoxy group, an ethoxy group, and a propoxy group. In this regard, however, it should be appreciated that the present invention is not limited thereto.

Examples of the aryloxy group represented by $R_3$ include a phenoxy group. In this regard, however, it should be appreciated that the present invention is not limited thereto.

In the formula (1), $R_4$ represents a hydrogen atom or an alkyl group having 1 to 4 carbon atoms.

Examples of the alkyl group represented by $R_4$ include a methyl group, an ethyl group, an n-propyl group, an isopropyl group, an n-butyl group, and a tert-butyl group. In this regard, however, it should be appreciated that the present invention is not limited thereto.

In the formula (1), $R_5$ and $R_6$ each represent an alkyl group having 1 to 4 carbon atoms.

Examples of the alkyl group represented by each of $R_5$ and $R_6$ include a methyl group, an ethyl group, an n-propyl group, an isopropyl group, an n-butyl group, and a tert-butyl group. In this regard, however, it should be appreciated that the present invention is not limited thereto.

In the formula (1), M represents Ir or Pt.

In the formula (1), a and b each represent an integer, provided that, when M represents Ir, it is necessary that the following requirements (A1) and (A2) are satisfied for a and b.

(A1) a+b=3

(A2) a represents 2 or 3

In addition, when M represents Pt, it is necessary that the following requirements (B1) and (B2) are satisfied for a and b.

(B1) a+b=2

(B2) a represents 1 or 2

Of the organic metal complexes of the present invention, an embodiment mode further satisfying the following requirement (C1) is preferred.

(C1) $R_1$, $R_2$, and $R_4$ each represent a hydrogen atom

In addition, of the organic metal complexes of the present invention, an embodiment mode further satisfying the following requirement (C2) is preferred.

(C2) $R_3$ represents a hydrogen atom or an alkyl group having 1 to 4 carbon atoms Further, of the organic metal complexes of the present invention, an embodiment mode satisfying the requirements (C1) and (C2) is particularly preferred.

Next, a method of synthesizing the organic metal complex of the present invention is described. It should be noted that the synthesis method described below is merely a specific example and the present invention is not limited thereto.

Upon synthesis of the organic metal complex of the present invention, at least the following ligand (i) needs to be prepared in advance. The following two kinds of ligands (i) and (ii) may be prepared.

(i) A ligand formed of a xanthone structure and a pyridine structure bonded to each other by a single bond (ii) An acetylacetone derivative Here, a method of synthesizing the ligand (i) is described below. The ligand (i) is synthesized by, for example, the following synthesis scheme.

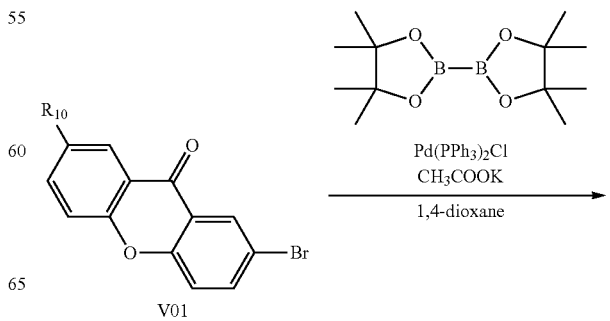

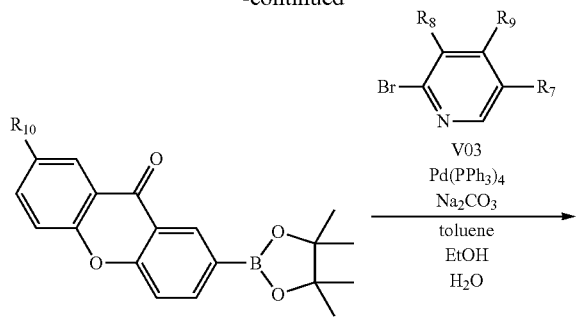

In the synthesis scheme, a substituent can be appropriately introduced to each of $R_7$ to $R_{10}$. Here, specific examples of the substituent that can be introduced to each of $R_7$ to $R_{10}$ are as described below.

(a) $R_7$: a hydrogen atom or an alkyl group having 1 to 4 carbon atoms (b) $R_8$: a hydrogen atom or an alkyl group having 1 to 4 carbon atoms (c) $R_9$: a hydrogen atom, an alkyl group having 1 to 4 carbon atoms, an alkoxy group having 1 to 6 carbon atoms, or an aryloxy group (d) $R_{10}$: a hydrogen atom or an alkyl group having 1 to 4 carbon atoms Next, a synthesis example of the organic metal complex is described. The organic metal complex of the present invention can be synthesized by, for example, the following synthesis scheme.

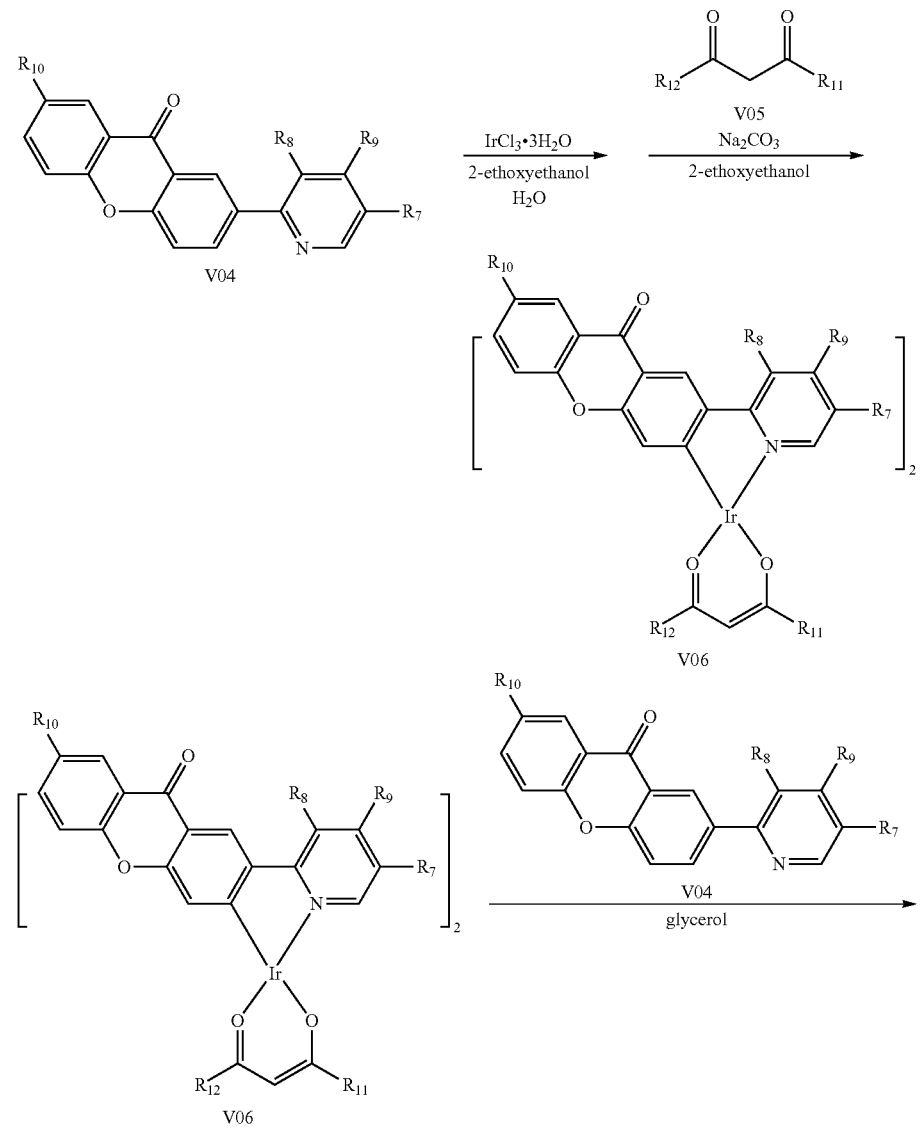

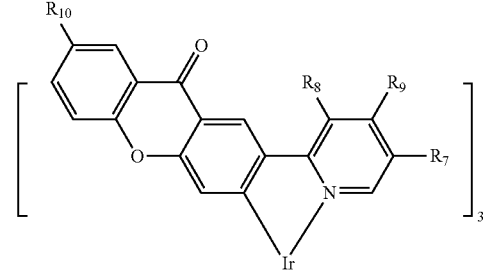

It should be noted that in the synthesis scheme, a substituent can be appropriately introduced to each of $R_7$ to $R_{10}$. Various indium complexes can be synthesized by appropriately introducing a substituent to each of $R_7$ to $R_{10}$ as described above. In addition, in the synthesis scheme, a substituent can be appropriately introduced to each of $R_{11}$ and $R_{12}$. Specifically, an alkyl group having 1 to 4 carbon atoms can be introduced.

In addition, as shown in the synthesis scheme, an iridium complex to which three ligands (i) coordinate can be synthesized by causing the compound V06 and the compound V04 (ligand) to react with each other in glycerol at a high temperature.

In addition, as in the iridium complex, with regard to a platinum complex, a platinum complex having only the ligand (i) or a platinum complex having the ligands (i) and (ii) can be synthesized. An example of the synthesis scheme is shown below.

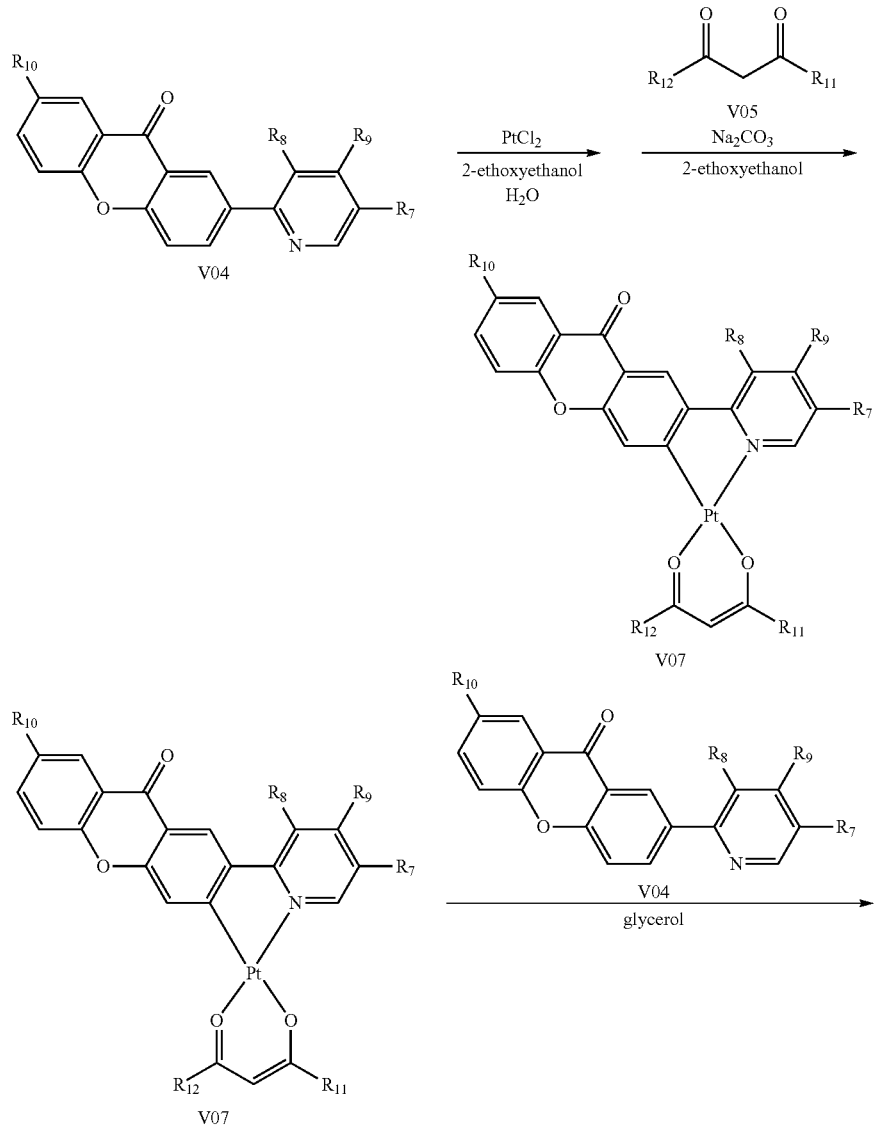

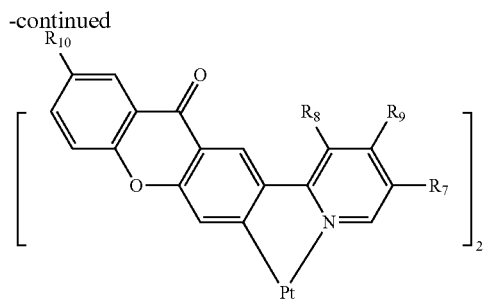

Next, the nature of the organic metal complex of the present invention is described. The organic metal complex of the present invention is a compound excellent in luminescence properties in blue luminescence. The term "blue luminescence" as used herein specifically refers to such luminescence that the peak wavelength of an emission spectrum is 430 nm to 480 nm. In addition, the phrase "excellent in luminescence properties" means that a luminescence quantum yield in a solution at room temperature is high. Specifically, according to NPL 3, the quantum yield of fac-Ir(ppy)$_3$ shown below as a metal complex representative of an iridium trischelate complex is 0.4. Accordingly, it can be said that a compound having a quantum yield higher than the foregoing has good luminescence properties.

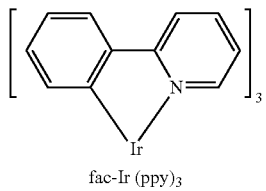

fac-Ir (ppy)$_3$

The organic metal complex of the present invention uses a ligand using 2-(pyridin-2-yl)-xanthone as a basic structure (hereinafter, sometimes referred to as "primary ligand"). Hereinafter, an action and effect for which the basic structure is directly or indirectly involved is described in detail.

Nature of Xanthone

A xanthone structure in the primary ligand has a high electron affinity because the structure has a carbonyl group as an electron-withdrawing group. In addition, xanthone alone has a triplet energy as high as 3.02 eV (410 nm). It should be noted that the triplet energy of a ligand to which no substituent has been introduced out of such primary ligands is 2.85 eV (435 nm).

Action and Effect of Primary Ligand in Organic Metal Complex

When the primary ligand is introduced to an organic metal complex (specifically, as a ligand for an iridium complex or a platinum complex), the electron density of the central metal of the organic metal complex can be reduced by the high electron affinity which xanthone in the primary ligand has. Accordingly, the HOMO level of the organic metal complex can be effectively deepened. As a result, the band gap of the organic metal complex widens. For example, an exemplary compound C01 as the organic metal complex of the present invention shown below shows blue luminescence having a wavelength of 470 nm while fac-Ir(ppy)$_3$ shows green luminescence having a wavelength of 510 nm.

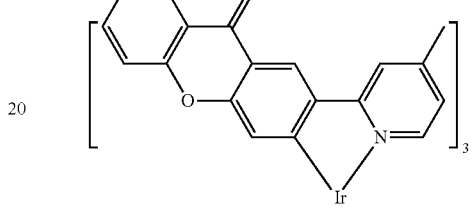

Position at which Pyridine is Bonded to Xanthone

The primary ligand in the organic metal complex of the present invention has xanthone and pyridine in its basic structure. Here, in consideration of the position at which pyridine is bonded to xanthone, several compounds obtained by the bonding of xanthone and pyridine are conceivable. Here, the inventors have paid attention to 2-(pyridin-2-yl)-xanthone as a compound obtained by bonding the carbon at the 2-position of xanthone and the carbon at the 2-position of pyridine with a single bond. In addition, the inventors have found that 2-(pyridin-2-yl)-xanthone as a compound serving as the basic structure of the primary ligand can reduce the electron density of the central metal of the organic metal complex. In addition, the inventors have found that an organic metal complex containing 2-(pyridin-2-yl)-xanthone shows luminescence having the shortest wavelength.

The reason for the foregoing is that the substitution position of a carbonyl group in the xanthone structure is important for an effective reduction in electron density of the central metal of the organic metal complex. A Hammet constant known as an indicator of the strength of the electron-withdrawing property of a substituent shows that a carbonyl group shows the strongest electron-withdrawing property when bonded to a para position. In other words, when (a bonding position with) the central metal and a carbonyl group are in a para positional relationship, the electron density of the central metal can be reduced most effectively. That is, it can be said that the bonding position of xanthone in the primary ligand with pyridine is such a bonding position that the emission wavelength of the organic metal complex itself can be made shortest.

It should be noted that the compound Z02 described in NPL 2 is given as an example in which (a bonding position with) the central metal and a carbonyl group are in a para positional relationship, though the compound is of a structure different from that of the organic metal complex of the present invention. The emission wavelength of the compound is 477 nm at 77 K. Meanwhile, the emission wavelength of fac-Ir(ppy)$_3$ not substituted with any carbonyl group is 510 nm. Accordingly, it is shown that the emission wavelength is shortened by the electron-withdrawing property which the introduced carbonyl group has. However, the emission wavelength needs to be further shortened in order that blue luminescence having a good purity can be achieved in a solution at room temperature. In contrast, the exemplary compound C01 as the organic metal complex of the present invention shows an emission wavelength of 470 nm in a solution at room temperature and has an improved color purity.

Substituent to be Introduced to Primary Ligand

As represented by the formula (1), substituents can be introduced to predetermined positions ($R_1$ to $R_4$) of the primary ligand of the organic metal complex of the present invention.

Here, intermolecular interaction can be suppressed by introducing an alkyl group to $R_1$ to $R_3$ in the formula (1). As a result, the solubility, sublimation property, and amorphous property in a thin-film state of the complex can be improved. However, the sublimation property reduces when the number of carbon atoms of the alkyl group is excessively large. Accordingly, the alkyl group to be introduced to $R_1$ to $R_3$ is desirably an alkyl group having 1 to 4 carbon atoms.

Meanwhile, the planarity of the xanthone structure can be reduced by introducing an alkyl group to $R_4$ in the formula (1). As a result, the intermolecular interaction resulting from a n-electron which the xanthone structure has can be suppressed, and hence the solubility, the sublimation property, and the amorphous property in a thin-film state can be improved. However, the sublimation property reduces when the number of carbon atoms of the alkyl group is excessively large. Accordingly, the alkyl group to be introduced to $R_4$ is desirably an alkyl group having 1 to 4 carbon atoms.

It should be noted that an unnecessary side reaction can be suppressed by introducing a substituent such as an alkyl group to $R_2$ or $R_4$ because $R_2$ positioned at the para position with respect to the ethereal oxygen of xanthone is susceptible to an electrophilic reaction.

In addition, an alkoxy group or an aryloxy group may be introduced to $R_3$ in the formula (1). The introduction of an alkoxy group or an aryloxy group to $R_3$ can effectively shallow the LUMO level of the organic metal complex. As a result, the energy gap involved in luminescence widens and hence the shortening of the emission wavelength can be realized.

When the ligands of the organic metal complex of the present invention are formed of a combination of the primary ligand and an acetylacetone derivative, $R_5$ and $R_6$ in the formula (1), which are substituents to be each independently selected, are preferably the same substituent from the viewpoint of the simplicity of the synthesis of the material. In addition, as the steric hindrance of a substituent enlarges, the intermolecular interaction can be suppressed to a larger extent, and hence the solubility, the sublimation property, and the amorphous property in a thin-film state can be improved. However, the sublimation property reduces when the number of carbon atoms of the alkyl group is excessively large. Accordingly, the alkyl group to be introduced to each of $R_5$ and $R_6$ is desirably an alkyl group having 1 to 4 carbon atoms.

As described above, the organic metal complex of the present invention can be used as a blue light emitting material, more specifically, a blue phosphorescent light emitting material. Accordingly, the complex can be preferably used as a light emitting material for an organic electroluminescence device. It should be noted that the organic electroluminescence device is described later. In addition, the organic metal complex of the present invention has a band gap wide enough to emit blue phosphorescence. Accordingly, the complex may be used as a host in a luminescent layer having, as a guest, a light emitting material that emits light with a color having a narrower band gap than the foregoing such as green light or red light.

Next, specific examples of the organic metal complex of the present invention are shown in Table 1 to Table 4 below, provided that the metal complexes shown in Table 1 to Table 4 are merely specific examples and the present invention is not limited to these metal complexes.

TABLE 1

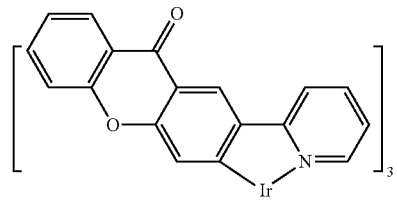

A01

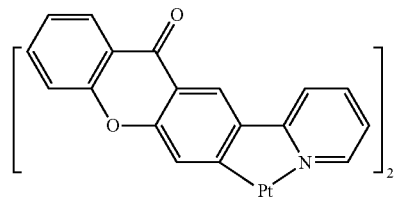

A02

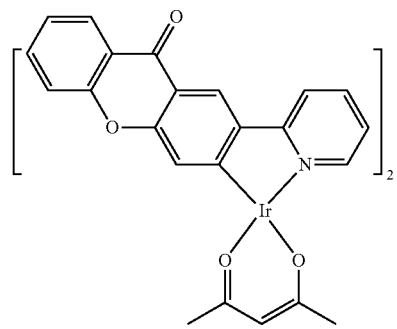

B01

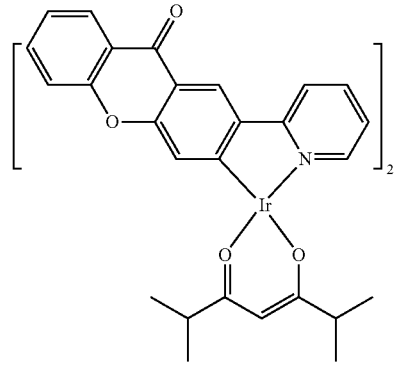

B02

TABLE 1-continued
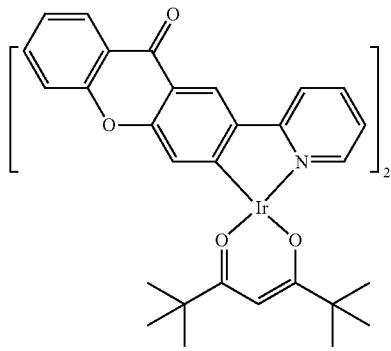 B03
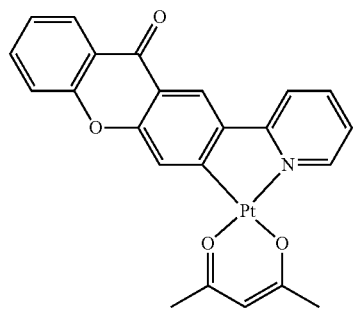 B04
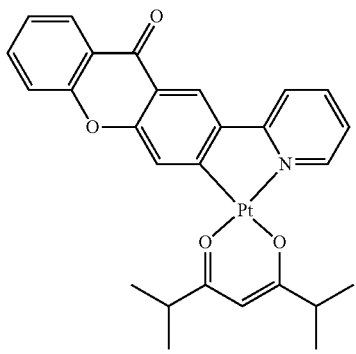 B05
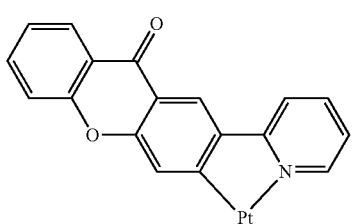 B06
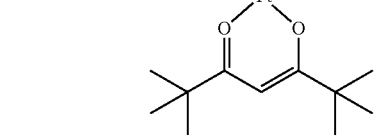 C01
TABLE 1-continued
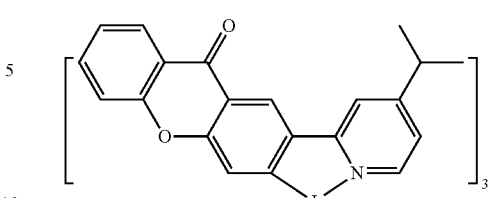 C02
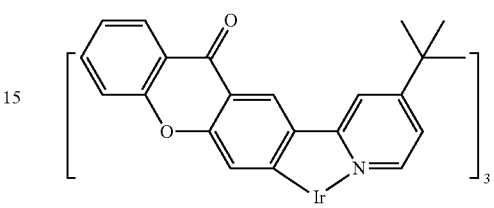 C03
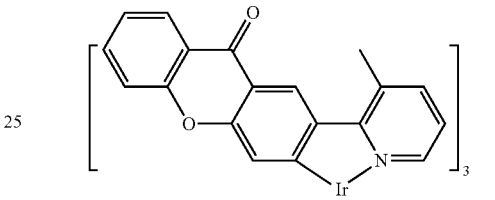 C04
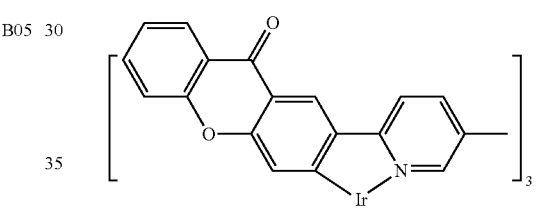 C05
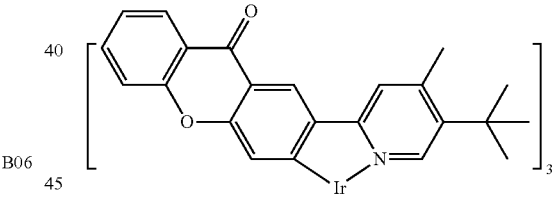 C06
TABLE 2
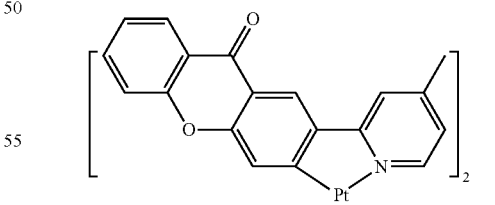 C07
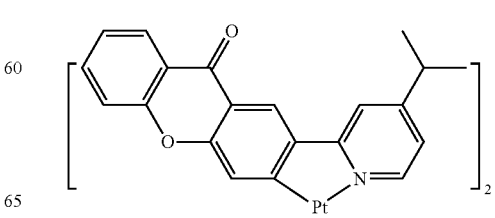 C08

TABLE 2-continued
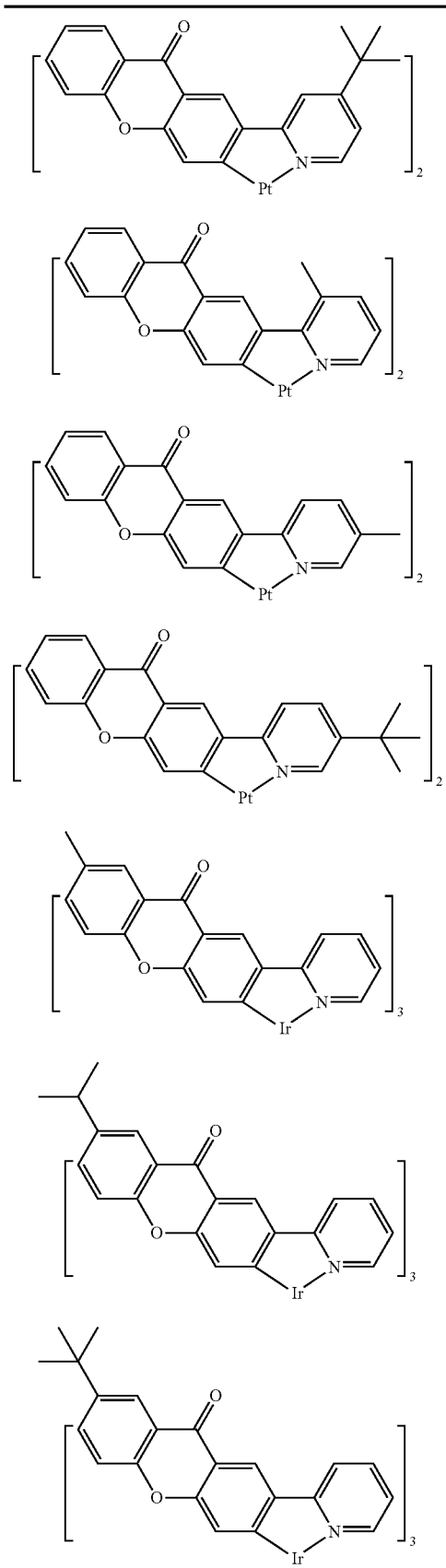
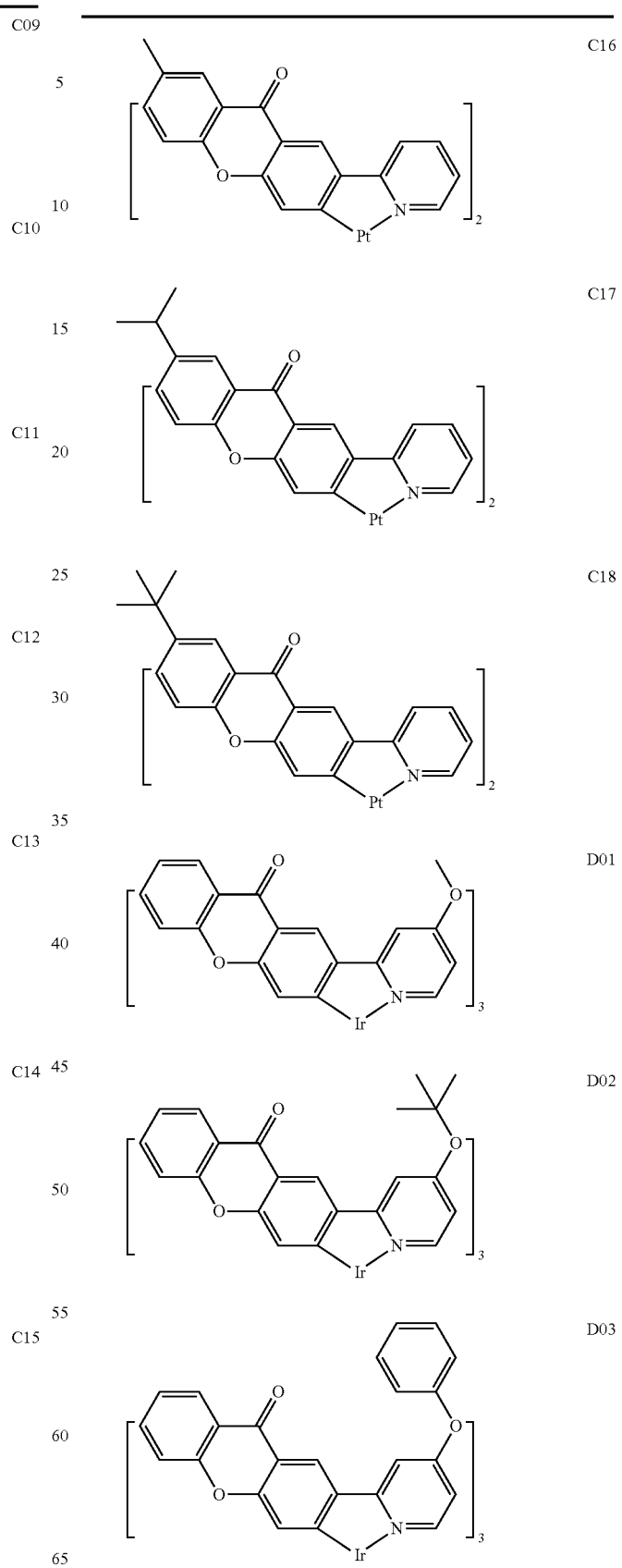

TABLE 3
| | |
|---|---|
| 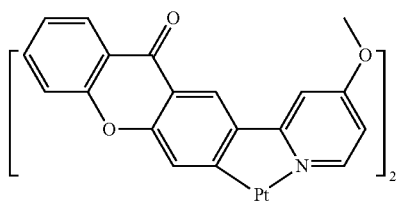 | D04 |
| 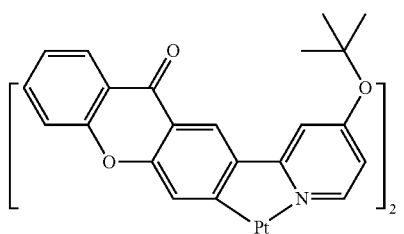 | D05 |
| 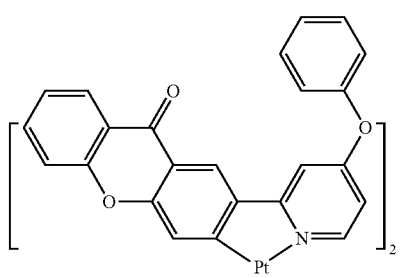 | D06 |
| 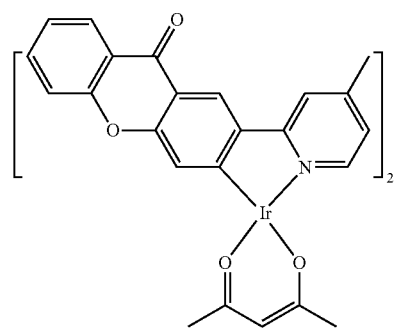 | E01 |
| 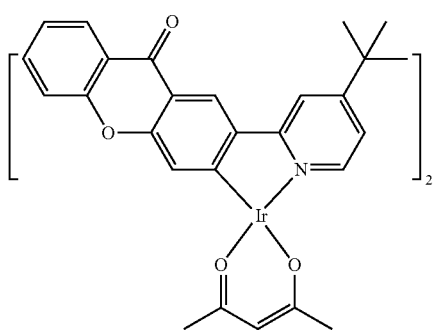 | E02 |
TABLE 3-continued
| | |
|---|---|
| 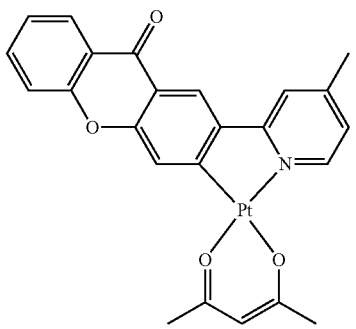 | E03 |
| 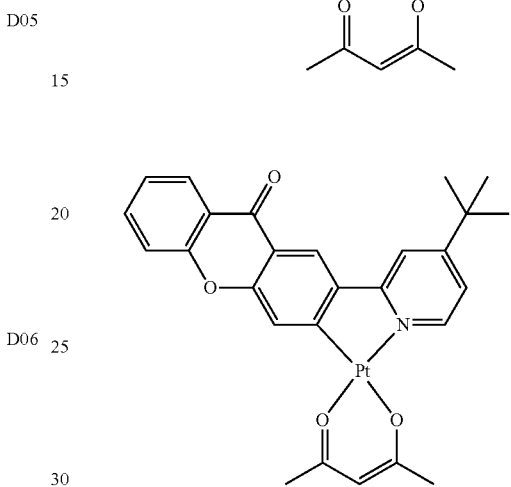 | E04 |
| 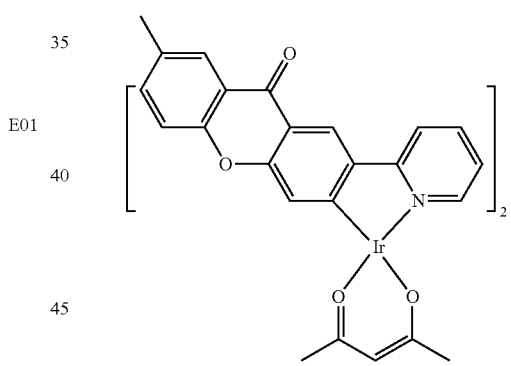 | E05 |
| 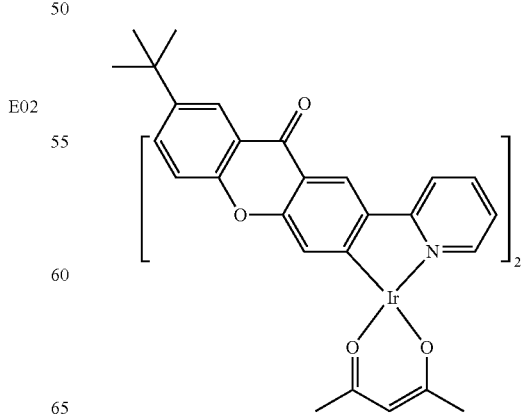 | E06 |

TABLE 3-continued
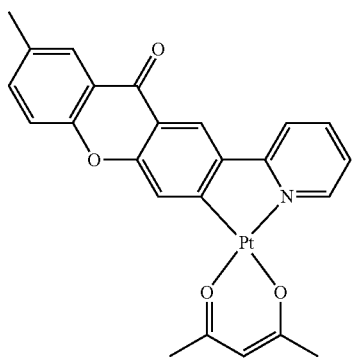
E07
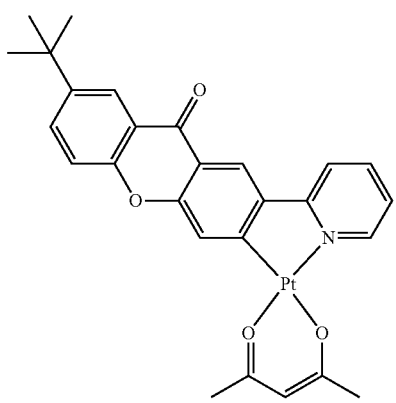
E08
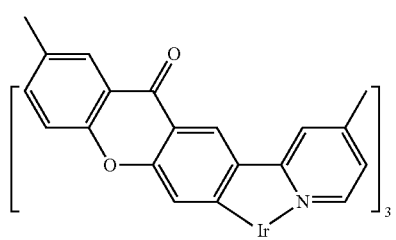
E09
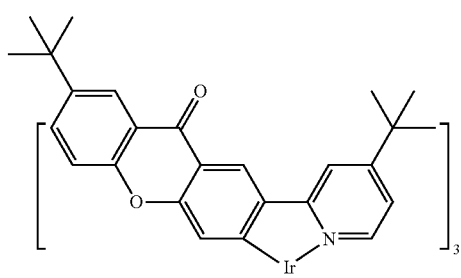
E10
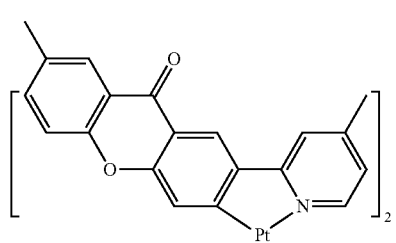
E11
TABLE 3-continued
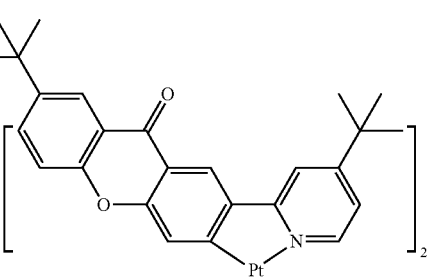
E12
TABLE 4
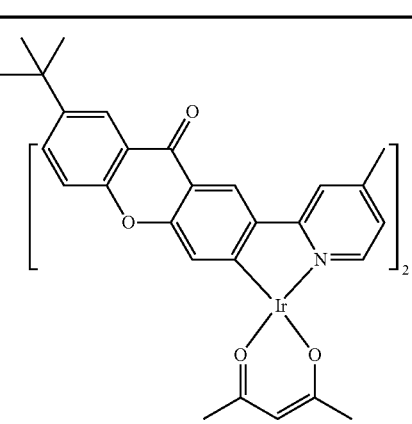
E13
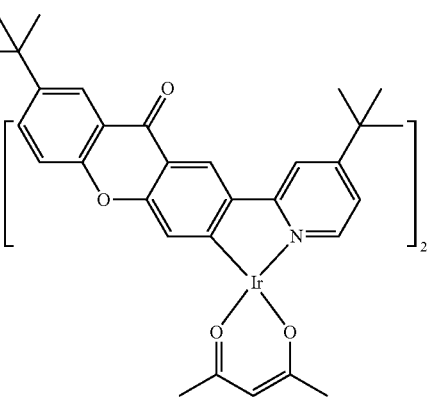
E14
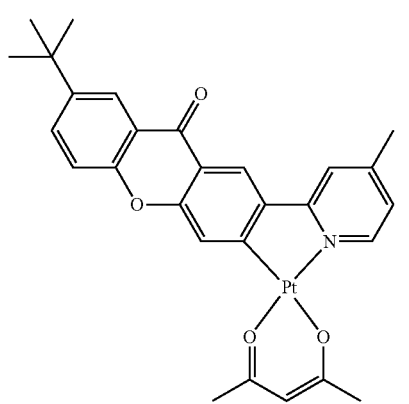
E15

TABLE 4-continued
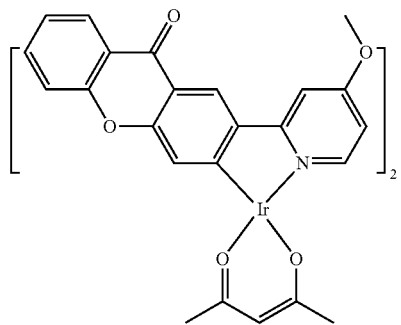 F01
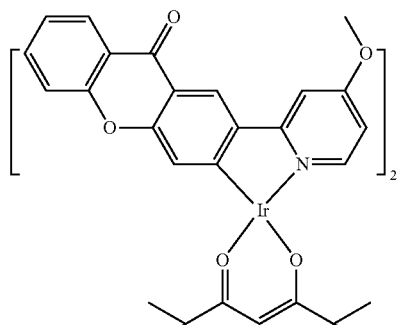 F02
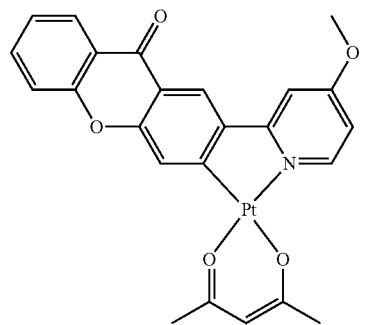 F03
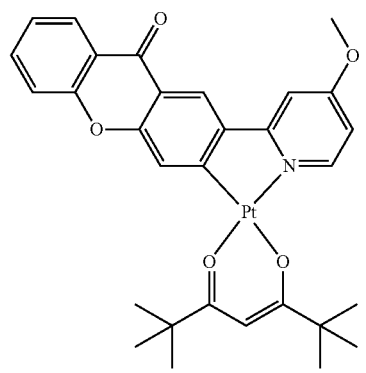 F04
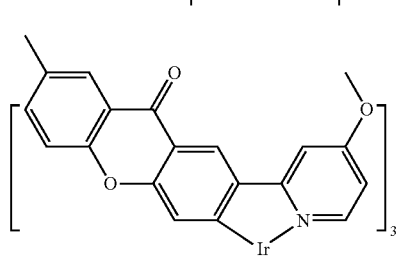 F05
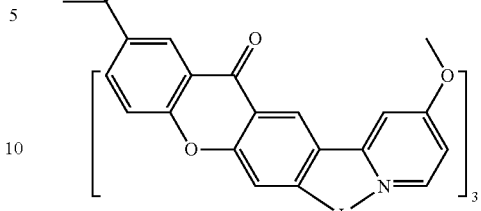 F06
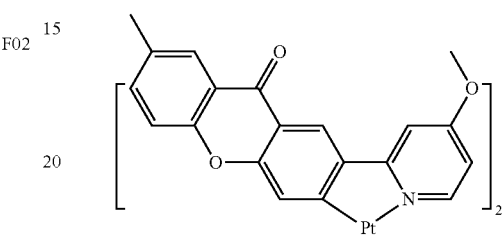 F07
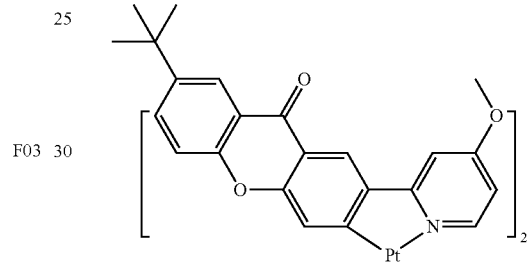 F08
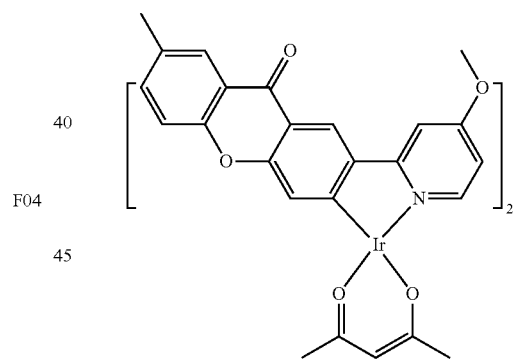 F09
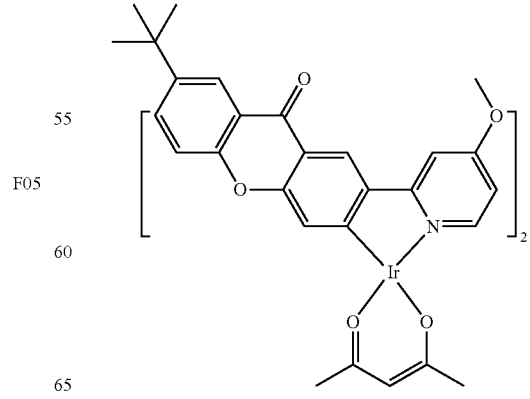 F10

TABLE 4-continued

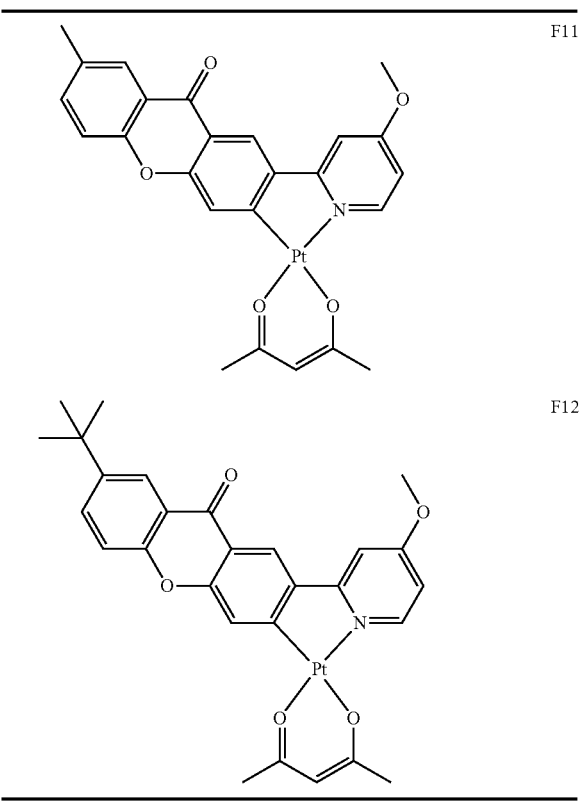

Of the exemplary organic metal complexes, each organic metal complex belonging to the group A is such that no substituent is present in the basic structure (xanthone-pyridine structure) of the primary ligand. Accordingly, the compound belonging to the group A has such an advantage that the compound can be easily synthesized. In addition, the organic metal complex belonging to the group A can provide good luminescence properties when used as a light emitting material for an organic electroluminescence device because the destabilization of the material resulting from the introduction of a substituent into the basic structure can never occur.

Of the exemplary organic metal complexes, each organic metal complex belonging to the group B contains an acetylacetone derivative as an auxiliary ligand in addition to the primary ligand. Here, the organic metal complex containing the acetylacetone derivative can be easily synthesized because the synthesis does not require any high temperature. In addition, the temperature of its sublimation purification can be significantly lowered by virtue of the nature of the acetylacetone derivative, that is, the small molecular weight of the compound itself and the reduction of the intermolecular interaction by an alkyl group.

Of the exemplary organic metal complexes, each organic metal complex belonging to the group C is such that an alkyl group is introduced as a substituent into the basic structure of the primary ligand. Here, the intermolecular interaction of the organic metal complex belonging to the group C is suppressed by steric hindrance caused by the alkyl group introduced into the basic structure of the primary ligand. Accordingly, the sublimation temperature of the complex itself can be lowered. In addition, in the case of such an organic metal complex that an alkyl group is introduced to a pyridine moiety, the reduction potential of the ligand increases by the introduction of the alkyl group, and hence a shortening effect on its emission wavelength is exerted.

Of the exemplary organic metal complexes, each organic metal complex belonging to the group D is such that an alkoxy group is introduced to a specific position ($R_3$) of the basic structure of the primary ligand. Here, the reduction potential of the ligand of the organic metal complex belonging to the group D can be increased by the alkoxy group as an electron-donating substituent. Accordingly, its emission wavelength can be further shortened.

Of the exemplary organic metal complexes, each organic metal complex belonging to the group E is such that the natures of the group B and the group C improving the sublimation property are combined. Here, the organic metal complex belonging to the group E is provided with the natures of the group B and the group C improving the sublimation property, specifically, an alkyl group causing steric hindrance and an acetylacetone derivative reducing the molecular weight of the entire compound. Accordingly, the sublimation property of the complex itself is significantly improved.

Of the exemplary organic metal complexes, each organic metal complex belonging to the group F is such that the natures of the group D exerting a shortening effect on the emission wavelength and of the group B and the group C improving the sublimation property are combined. Accordingly, the organic metal complex belonging to the group F can simultaneously achieve the shortening of the emission wavelength and the improvement of the sublimation property.

In addition, the emission wavelength of the organic metal complex of the present invention can be changed by appropriately introducing a substituent to the basic structure of the organic metal complex.

Next, an organic electroluminescence device of the present invention is described. The organic electroluminescence device of the present invention is constituted of: a pair of electrodes; and an organic compound layer that is arranged between the pair of electrodes and having at least a luminescent layer. The term "pair of electrodes" as used herein refers to, for example, a pair of electrodes formed of an anode and a cathode. It should be noted that in the present invention, an electric field in a reverse direction as well as a necessary electric field in a forward direction may be applied to the pair of electrodes for the purpose of causing the device to emit light.

The organic compound layer in the organic electroluminescence device of the present invention is a single layer or a laminate formed of multiple layers having at least a luminescent layer. A layer constituting the organic compound layer except the luminescent layer is, for example, a hole injection layer, a hole transporting layer, a hole-exciton blocking layer, an electron transporting layer, or an electron injection layer, provided that the present invention is not limited thereto.

A combination of the organic compound layer having the organic metal complex according to the present invention and another organic compound layer can be appropriately selected. The number of the other organic compound layers may be two or more.

Specific examples of the layer construction of the organic compound layer in the organic electroluminescence device of the present invention are listed below. It should be noted that in Specific Example 2 out of the specific examples listed below, at least one of the hole transporting layer and the electron transporting layer has a function as a luminescent layer.

Specific Example 1

(anode/)luminescent layer(/cathode)

Specific Example 2

(anode/)hole transporting layer/electron transporting layer (/cathode)

Specific Example 3

(anode/)hole transporting layer/luminescent layer/electron transporting layer(/cathode)

Specific Example 4

(anode/)hole injection layer/hole transporting layer/luminescent layer/electron transporting layer(/cathode)

Specific Example 5

(anode/)/hole transporting layer/luminescent layer/hole-exciton blocking layer/electron transporting layer(/cathode)

It should be noted that the constructions of Specific Example 1 to Specific Example 5 merely show fundamental constructions of the organic compound layer, and the present invention is by no means limited to those specific examples.

In the present invention, the organic metal complex of the present invention is incorporated into the organic compound layer, more specifically, any one of the layers constituting the organic compound layer. Of the layers constituting the organic compound layer, the layer having the organic metal complex of the present invention is, for example, a hole injection layer, a hole transporting layer, the luminescent layer, a hole-exciton blocking layer, an electron transporting layer, or an electron injection layer. Of those, the luminescent layer is preferred.

When the organic metal complex of the present invention is incorporated into the luminescent layer, the luminescent layer may be a layer formed only of the organic metal complex of the present invention, or may be a layer formed of a host and a guest. The luminescent layer is preferably a layer formed of a host and a guest. Here, when the luminescent layer is a layer formed of a host and a guest, the guest is preferably the organic metal complex of the present invention in consideration of the properties (luminescence properties) of a material itself of the organic metal complex of the present invention. Here, the organic metal complex of the present invention is particularly preferably used as a guest in a luminescent layer constituting a blue electroluminescence device.

By the way, the host and the guest in the luminescent layer are each defined by the weight ratio of a compound constituting the luminescent layer. That is, a compound having the largest weight ratio out of the compounds constituting the luminescent layer is the host. On the other hand, a compound having a weight ratio smaller than that of the host out of the compounds constituting the luminescent layer is the guest. Here, the content of the guest in the luminescent layer is preferably 0.01 wt % or more and 20 wt % or less, more preferably 0.5 wt % or more and 10 wt % or less with reference to the total weight of the luminescent layer. In addition, the guest is preferably a light emitting material that determines the luminescent color of the organic electroluminescence device. Meanwhile, when the luminescent layer has multiple kinds (three or more kinds) of organic compounds, a luminescence assisting material, a charge injection material, or the like may be incorporated as a material other than the host and the guest into the luminescent layer.

It should be noted that when the organic metal complex of the present invention is used as the guest for the luminescent layer, a material having a lowest unoccupied molecular orbital level (LUMO level) higher than that of the organic metal complex of the present invention, in other words, a host having an LUMO level closer to a vacuum level is preferably used as the host. This is because the organic metal complex of the present invention has a low LUMO level and hence can better receive an electron to be supplied to the luminescent layer, i.e. the host, from the host.

Next, a constituent material for the organic electroluminescence device of the present invention except the organic metal complex of the present invention is described.

An organic compound constituting a hole injection layer or a hole transporting layer is preferably a compound having a high hole mobility. In this case, the organic compound may be a low-molecular weight compound, or may be a high-molecular weight compound. The organic compound is exemplified by a triarylamine derivative, a phenylenediamine derivative, a stilbene derivative, a phthalocyanine derivative, a porphyrin derivative, poly(vinylcarbazole), poly(thiophene), and other conductive polymers. Here, specific examples of the organic compound constituting a hole injection layer or a hole transporting layer are shown below.

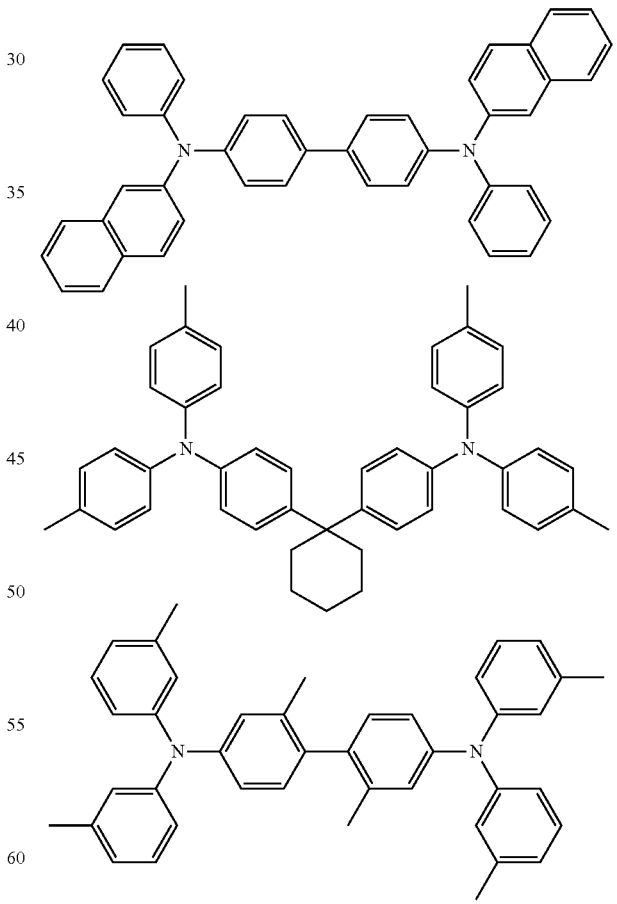

An organic compound constituting an electron injection layer or an electron transporting layer is selected in consideration of a balance with the hole mobility of the compound in the injection layer or the hole transporting layer. The organic compound is exemplified by an oxadiazole derivative, an oxazole derivative, a pyrazine derivative, a triazole derivative, a triazine derivative, a quinoline derivative, a quinoxaline derivative, a phenanthroline derivative, and an organic aluminum complex. Here, specific examples of the organic compound constituting an electron injection layer or an electron transporting layer are shown below.

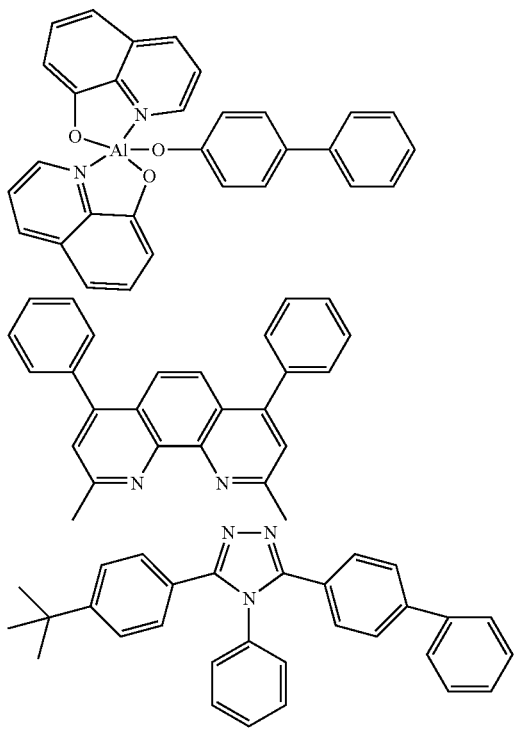

The host in the organic electroluminescence device of the present invention is preferably a material that enables good movement of each of a hole and an electron as carriers. In addition, the host is more preferably a material having a lowest triplet excitation energy level $T_1$ higher than that of the light emitting material in order that an exciton produced in the luminescent layer may be efficiently utilized for luminescence. Examples of the host include a fused ring compound (such as a fluorene derivative, a naphthalene derivative, a carbazole derivative, a quinoxaline derivative, or a quinoline derivative), an organic aluminum complex such as tris(8-quinolinolato)aluminum, an organic zinc complex, a triphenylamine derivative, and a polymer derivative such as a poly(fluorene) derivative or a poly(phenylene) derivative. Specific examples of the organic compounds each to be used as the host of the luminescent layer in this case are shown below.

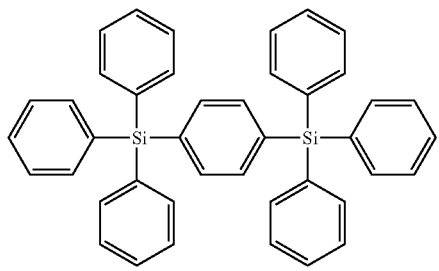

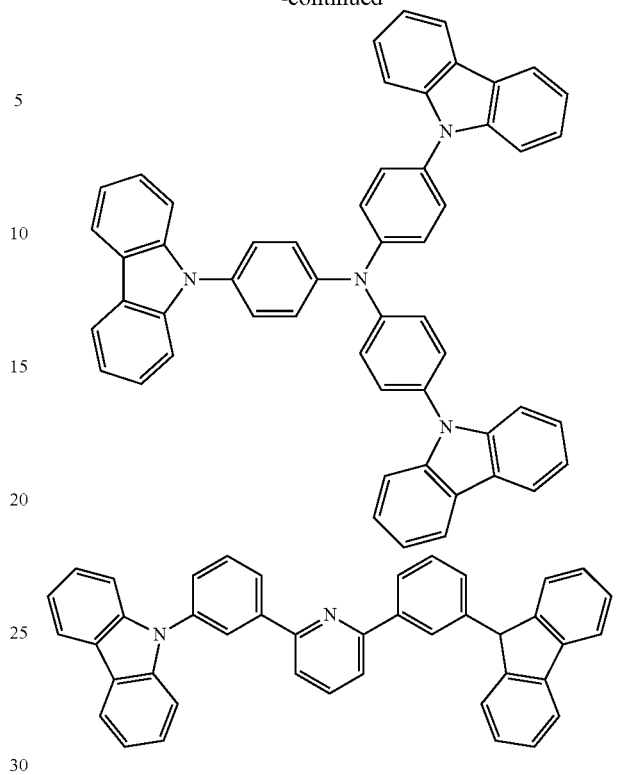

It is recommended that a material for constituting an anode have as large a work function as possible. Examples of the material include, as the material for constituting an anode, a simple metal material such as gold, platinum, silver, copper, nickel, palladium, cobalt, selenium, vanadium, or tungsten, an alloy including a combination of multiple kinds of those metals, and a metal oxide such as tin oxide, zinc oxide, indium oxide, indium tin oxide (ITO), or indium zinc oxide. Further, a conductive polymer such as polyaniline, polypyrrole, or polythiophene may also be used. One kind of those electrode substances may be used alone, or multiple kinds thereof may be used in combination. Further, the anode may be constituted of a single layer or may be constructed of multiple layers.

It is recommended that a material for constituting a cathode have a small work function. Examples of the material include alkali metals such as lithium, alkaline earth metals such as calcium, and metal elements such as aluminum, titanium, manganese, silver, lead, and chromium. Alternatively, an alloy including a combination of multiple kinds of those metal elements may also be used. For example, as the alloy, magnesium-silver, aluminum-lithium, or aluminum-magnesium may be used. A metal oxide such as indium tin oxide (ITO) may also be utilized. One kind of those electrode substances may be used alone, or multiple kinds thereof may be used in combination. Further, the cathode may be constituted of a single layer or may be constructed of multiple layers.

A layer containing the organic metal complex of the present invention and a layer formed of another organic compound are formed by the following method. A thin film is formed by a vacuum vapor deposition method, an ionization vapor deposition method, a sputtering method, a plasma method, or a coating method (for example, a spin coating method, a dipping method, a casting method, an LB method, or an ink jet method) involving dissolving the material in an appropriate solvent and coating the resultant. When the layer is formed by a vacuum vapor deposition method, a solution coating method, or the like, the layer is hard to undergo crystallization or the like and is excellent in stability over time. Further, when the film is formed by a coating method, the film may also be formed in combination with an appropriate binder resin.

Examples of the binder resin include, but not limited to, a poly(vinylcarbazole) resin, a polycarbonate resin, a polyester resin, an ABS resin, an acrylic resin, a polyimide resin, a phenolic resin, an epoxy resin, a silicon resin, and a urea resin.

Further, one kind of those binder resins may be used alone as a homopolymer or copolymer, or two or more kinds thereof may be used as a mixture. In addition, a known additive such as a plasticizer, an antioxidant, or an ultraviolet absorber may be used in combination, as necessary.

The organic electroluminescence device of the present invention can be used in a display device or an illumination device. Alternatively, the device can be used in, for example, an exposure light source for an electrophotographic image-forming device or the backlight of a liquid crystal display device.

Here, the display device has a display unit for displaying an image and an input unit for inputting image information. In addition, the display device is a device having the organic electroluminescence device of the present invention in the display unit. It should be noted that the display unit has multiple pixels. In addition, the pixels have the organic electroluminescence device of the present invention and a TFT element which is an example of a switching element for controlling the emission luminance of the organic electroluminescence device. The switching element serves also as an element provided for electrically connecting the anode or cathode constituting the organic electroluminescence device and the drain electrode or source electrode of a thin-film transistor.

The display device can be used as an image display device for a PC, a head mount display, a cellular phone, or the like. An image to be displayed may be a two-dimensional image, or may be a three-dimensional image.

The display device includes an input unit for inputting image information from an area CCD, a linear CCD, a memory card, or the like, and may be an image output device for outputting the input image to a display unit.

The image output device may be a digital camera using an imaging element such as a CCD sensor in the image input unit and having an imaging optical system.

The display device may have such an input function that input can be performed by touching an output image. The function is, for example, a touch panel function.

Further, the display device may be used for a display unit of a multifunction printer.

The organic electroluminescence device of the present invention may be used in an illumination device. The illumination device has an organic electroluminescence device of the present invention; and an inverter circuit connected to the organic electroluminescence device.

The color of the illumination light of the illumination device having the organic electroluminescence device of the present invention may be white, may be neutral white, or may be any other color.

Next, a display device using the organic electroluminescence device of the present invention is described with reference to the drawing.

FIGURE is a cross-sectional schematic diagram illustrating an example of a display device including an organic electroluminescence device of the present invention and a TFT element as an example of a switching element electrically connected to the organic electroluminescence device. It should be noted that an embodiment mode having two sets of the organic electroluminescence device and the TFT element is illustrated in a display device 20 of FIGURE. Details of the structure of the display device are described below.

The display device 20 of FIGURE includes a substrate 1 made of glass or the like and a moisture-barrier film 2 for protecting a TFT element or an organic compound layer on the substrate. Further, a gate electrode 3 made of metal is represented by reference numeral 3, a gate insulating film 4 is represented by reference numeral 4, and a semiconductor layer is represented by reference numeral 5.

A TFT element 8 includes the semiconductor layer 5, a drain electrode 6, and a source electrode 7. An insulating film 9 is provided above the TFT element 8. An anode 11 of the organic electroluminescence device is connected to the source electrode 7 via a contact hole (through hole) 10. It should be noted that the display device of the present invention is not limited to the construction of FIGURE, and it is enough that any one of the anode and a cathode is connected to any one of the source electrode and the drain electrode of the TFT element.

In the display device 20 of FIGURE, an organic compound layer 12, which is illustrated in a simplified form as a single layer, may actually be an organic compound layer formed of multiple layers. Provided on a cathode 13 are a first protective layer 14 and a second protective layer 15 for suppressing a reduction in performance of the organic electroluminescence device.

In the display device according to this embodiment, a switching element is not particularly limited, and a transistor or an MIM element may be used. A thin-film transistor using single crystal silicon, an amorphous silicon-type transistor element, or the like may be used as the transistor. The thin-film transistor is also referred to as "TFT element."

The emission luminance of the organic electroluminescence device is controlled by the switching element. When multiple organic electroluminescence devices are provided within a surface, an image can be displayed by virtue of their respective emission luminances.

Alternatively, the control can be performed by producing an active matrix driver on an Si substrate and providing the organic electroluminescence device on the driver.

The constitution depends on a definition. In the case of, for example, a definition of about a QVGA per inch, the organic electroluminescence device is preferably provided on the Si substrate.

An image with good quality can be stably displayed for a long time period by driving the display device using the organic electroluminescence device according to this embodiment.

EXAMPLES

Hereinafter, the present invention is described by way of examples. Note that the present invention is not limited thereto.

Example 1

Synthesis of Exemplary Compound E01

An exemplary compound E01 was synthesized according to the following synthesis scheme.

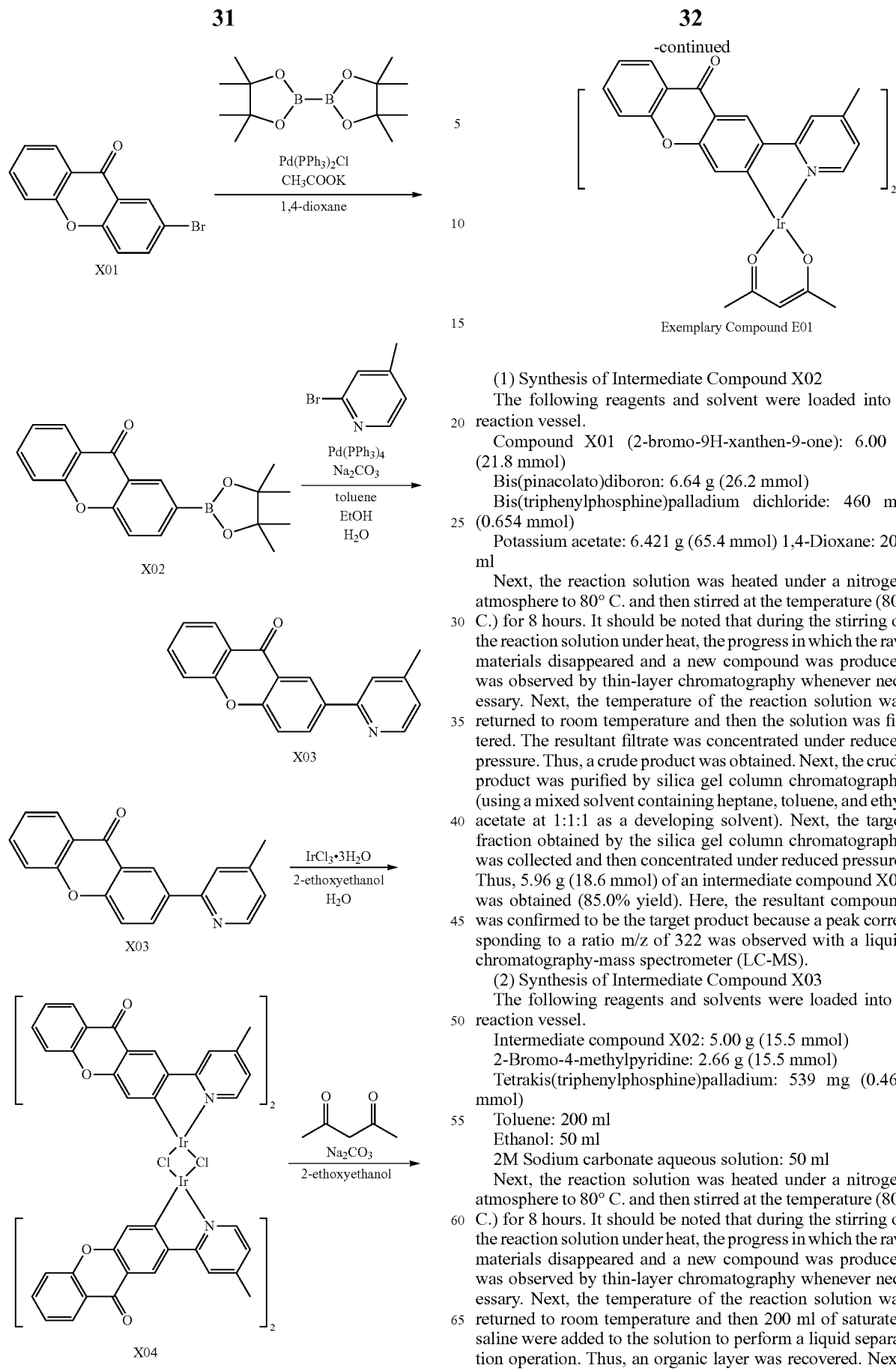

Exemplary Compound E01

(1) Synthesis of Intermediate Compound X02

The following reagents and solvent were loaded into a reaction vessel.

Compound X01 (2-bromo-9H-xanthen-9-one): 6.00 g (21.8 mmol)

Bis(pinacolato)diboron: 6.64 g (26.2 mmol)

Bis(triphenylphosphine)palladium dichloride: 460 mg (0.654 mmol)

Potassium acetate: 6.421 g (65.4 mmol) 1,4-Dioxane: 200 ml

Next, the reaction solution was heated under a nitrogen atmosphere to 80° C. and then stirred at the temperature (80° C.) for 8 hours. It should be noted that during the stirring of the reaction solution under heat, the progress in which the raw materials disappeared and a new compound was produced was observed by thin-layer chromatography whenever necessary. Next, the temperature of the reaction solution was returned to room temperature and then the solution was filtered. The resultant filtrate was concentrated under reduced pressure. Thus, a crude product was obtained. Next, the crude product was purified by silica gel column chromatography (using a mixed solvent containing heptane, toluene, and ethyl acetate at 1:1:1 as a developing solvent). Next, the target fraction obtained by the silica gel column chromatography was collected and then concentrated under reduced pressure. Thus, 5.96 g (18.6 mmol) of an intermediate compound X02 was obtained (85.0% yield). Here, the resultant compound was confirmed to be the target product because a peak corresponding to a ratio m/z of 322 was observed with a liquid chromatography-mass spectrometer (LC-MS).

(2) Synthesis of Intermediate Compound X03

The following reagents and solvents were loaded into a reaction vessel.

Intermediate compound X02: 5.00 g (15.5 mmol)

2-Bromo-4-methylpyridine: 2.66 g (15.5 mmol)

Tetrakis(triphenylphosphine)palladium: 539 mg (0.466 mmol)

Toluene: 200 ml

Ethanol: 50 ml

2M Sodium carbonate aqueous solution: 50 ml

Next, the reaction solution was heated under a nitrogen atmosphere to 80° C. and then stirred at the temperature (80° C.) for 8 hours. It should be noted that during the stirring of the reaction solution under heat, the progress in which the raw materials disappeared and a new compound was produced was observed by thin-layer chromatography whenever necessary. Next, the temperature of the reaction solution was returned to room temperature and then 200 ml of saturated saline were added to the solution to perform a liquid separation operation. Thus, an organic layer was recovered. Next, the organic layer was dried with anhydrous sodium sulfate and then concentrated under reduced pressure. Thus, a crude product was obtained. Next, the crude product was purified by silica gel column chromatography (using a mixed solvent containing heptane, toluene, and ethyl acetate at 5:2:1 as a developing solvent). Next, the target fraction obtained by the silica gel column chromatography was collected and then concentrated under reduced pressure. Thus, 3.84 g (13.4 mmol) of an intermediate compound X03 was obtained (86.1% yield). Here, the resultant compound was confirmed to be the target product because a peak corresponding to a ratio m/z of 287 was observed with a liquid chromatography-mass spectrometer (LC-MS).

(3) Synthesis of Intermediate Compound X04

The following reagents and solvents were loaded into a reaction vessel.

Iridium trichloride trihydrate: 500 mg (1.42 mmol)
Intermediate compound X03: 1.22 g (4.26 mmol)
2-Ethoxyethanol: 15 ml
Water: 5 ml Next, the reaction solution was heated under a nitrogen atmosphere to 100° C. and then stirred at the temperature (100° C.) for 12 hours. Next, the temperature of the reaction solution was returned to room temperature and then the precipitated solid was recovered by filtration. Next, the recovered residue was subjected to dispersion washing with 30 ml of methanol twice. Thus, 788 mg (0.492 mmol) of an intermediate compound X04 was obtained (69.3% yield). The resultant compound was confirmed to be the target product because a peak corresponding to a ratio m/z of 1,600 was observed by matrix-assisted laser desorption time-of-flight mass spectrometry (MALDI-TOF MS).

(4) Synthesis of Exemplary Compound E01

The following reagents and solvent were loaded into a reaction vessel.

Intermediate compound X04: 700 mg (0.437 mmol)
Acetylacetone: 437 mg (4.37 mmol)
Sodium carbonate: 463 mg (4.37 mmol)
2-Ethoxyethanol: 20 ml Next, the reaction solution was heated under a nitrogen atmosphere to 100° C. and then stirred at the temperature (100° C.) for 8 hours. Next, the temperature of the reaction solution was returned to room temperature and then the precipitated solid was recovered by filtration. Next, the recovered residue was subjected to dispersion washing with 20 ml of methanol twice, followed by purification by silica gel column chromatography (developing solvent: chloroform). Next, the target fraction obtained by the silica gel column chromatography was concentrated under reduced pressure and then recrystallized with toluene. Next, the solid precipitated by the recrystallization was recovered by filtration. Thus, 615 mg (0.711 mmol) of an exemplary compound E01 was obtained (81.3% yield). The resultant compound was confirmed to be the target product because a peak corresponding to a ratio m/z of 865 was observed by matrix-assisted laser desorption time-of-flight mass spectrometry (MALDI-TOF MS). In addition, 100 mg of the resultant exemplary compound E01 was subjected to sublimation purification with a sublimation purification system manufactured by ULVAC KIKO, Inc. It should be noted that during the sublimation purification, the degree of vacuum was set to $7.0 \times 10^{-1}$ Pa, the flow rate of an argon gas was set to 10 ml/min, and the sublimation temperature was set to 350° C. 78 milligrams of the exemplary compound E01 was obtained by the sublimation purification.

Meanwhile, the exemplary compound E01 obtained after the sublimation purification was confirmed to have a purity of 99.9% or more at a 254 nm absorption by high-performance liquid chromatography (HPLC) measurement.

On the other hand, a toluene solution of the exemplary compound E01 (concentration: $1 \times 10^{-5}$ mol/L) was prepared and then the emission spectrum of the toluene solution at an excitation wavelength of 300 nm was measured with an F-4500 manufactured by Hitachi, Ltd. As a result, its maximum emission wavelength was 484 nm. In addition, the quantum yield of the toluene solution measured with an absolute quantum yield meter (C9920-02 manufactured by Hamamatsu Photonics K.K.) was 0.60.

Further, thermal analysis measurement with a thermogravimetric/differential thermal analyzer (TG-DTA2000SA manufactured by Bruker) confirmed that no thermal decomposition occurred at 350° C.

Example 2

Synthesis of Exemplary Compound C01

An exemplary compound C01 was synthesized according to the following synthesis scheme.

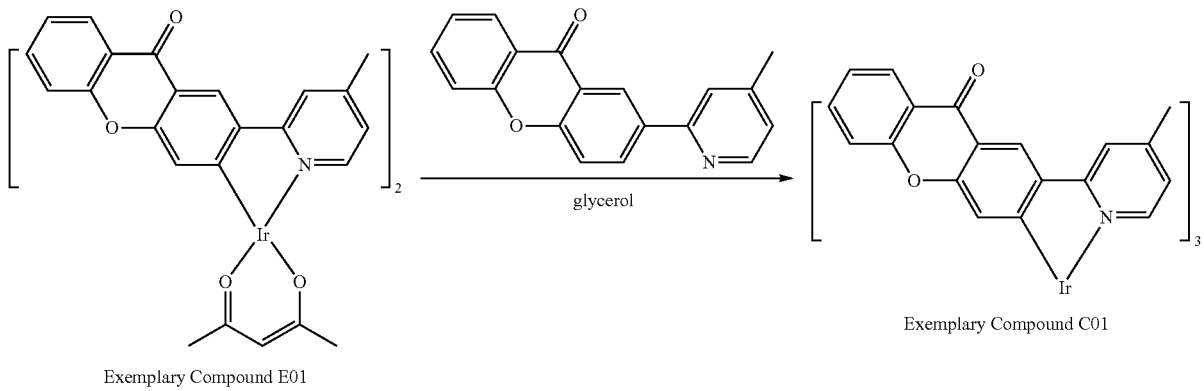

Exemplary Compound E01

Exemplary Compound C01

The following reagents and solvent were loaded into a reaction vessel.

Exemplary compound E01: 500 mg (0.578 mmol)
Intermediate compound X03: 498 mg (1.73 mmol)
Glycerol: 25 ml Next, the reaction solution was heated under a nitrogen atmosphere to 220° C. and then stirred at the temperature (220° C.) for 12 hours. Next, the temperature of the reaction solution was returned to room temperature and then 100 ml of water were added to the solution, and the resultant was further stirred. Next the precipitated solid was recovered by filtration. Thus, a crude product was obtained. Next, the product was subjected to purification by silica gel column chromatography (developing solvent: chloroform). Next, the target fraction obtained by the silica gel column chromatography was collected and concentrated under reduced pressure and then recrystallized with toluene. The solid precipitated by the recrystallization was recovered by filtration. Thus, 442 mg (0.421 mmol) of an exemplary compound C01 was obtained (72.8% yield). The resultant compound was confirmed to be the target product because a peak corresponding to a ratio m/z of 1,051 was observed by matrix-assisted laser desorption time-of-flight mass spectrometry (MALDI-TOF MS). In addition, the resultant complex was found to be a facial isomer because nine protons were assigned by $^1$H-NMR measurement.

In addition, 250 mg of the resultant exemplary compound C01 was subjected to sublimation purification with a sublimation purification system manufactured by ULVAC KIKO, Inc. It should be noted that during the sublimation purification, the degree of vacuum was set to $7.0 \times 10^{-1}$ Pa, the flow rate of an argon gas was set to 10 ml/min, and the sublimation temperature was set to 450° C. 98 milligrams of the exemplary compound C01 was obtained by the sublimation purification.

Meanwhile, the exemplary compound C01 obtained after the sublimation purification was confirmed to have a purity in absorption at 254 nm of 99.9% or more by high-performance liquid chromatography (HPLC) measurement.

On the other hand, a toluene solution of the exemplary compound C01 (concentration: $1 \times 10^{-5}$ mol/L) was prepared and then the emission spectrum of the toluene solution at an excitation wavelength of 300 nm was measured with an F-4500 manufactured by Hitachi, Ltd. As a result, its maximum emission wavelength was 470 nm. In addition, the quantum yield of the toluene solution measured with an absolute quantum yield meter (C9920-02 manufactured by Hamamatsu Photonics K.K.) was 0.69.

Further, thermal analysis measurement with a thermogravimetric/differential thermal analyzer (TG-DTA2000SA manufactured by Bruker) confirmed that no thermal decomposition occurred at 450° C.

Example 3

Synthesis of Exemplary Compound D01

An exemplary compound D01 was synthesized by employing the methods of Examples 1 and 2 in combination except that the following compound X05 was used instead of the intermediate compound X03 in '(3)' of Example 1. It should be noted that the compound X05 can be synthesized by using 2-bromo-4-methoxypyridine instead of 2-bromo-4-methylpyridine in '(2)' of Example 1.

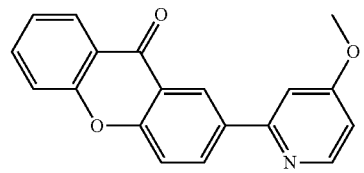

Luminescence properties were measured in the same manner as in Example 1. As a result, the maximum emission wavelength was 463 nm and the quantum yield was 0.58.

Example 4

Synthesis of Exemplary Compound C15

An exemplary compound C15 was synthesized by employing the methods of Examples 1 and 2 in combination except that the following compound X06 was used instead of the intermediate compound X03 in '(3)' of Example 1 (3).

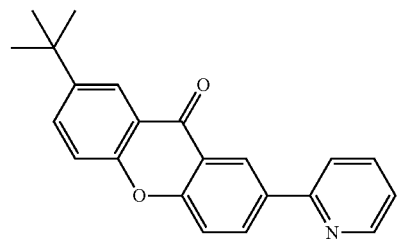

It should be noted that the compound X06 can be synthesized by using the following compound X01a instead of the compound X01 in '(1)' of Example 1 and by using 2-bromopyridine instead of 2-bromo-4-methylpyridine in '(2)' of Example 1.

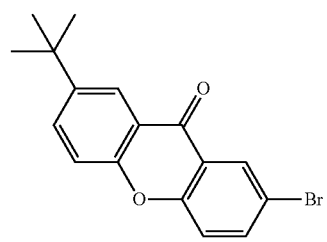

Luminescence properties were measured in the same manner as in Example 1. As a result, the maximum emission wavelength was 471 nm and the quantum yield was 0.70.

Example 5

Synthesis of Exemplary Compound E03

An exemplary compound E03 was synthesized according to the following synthesis scheme.

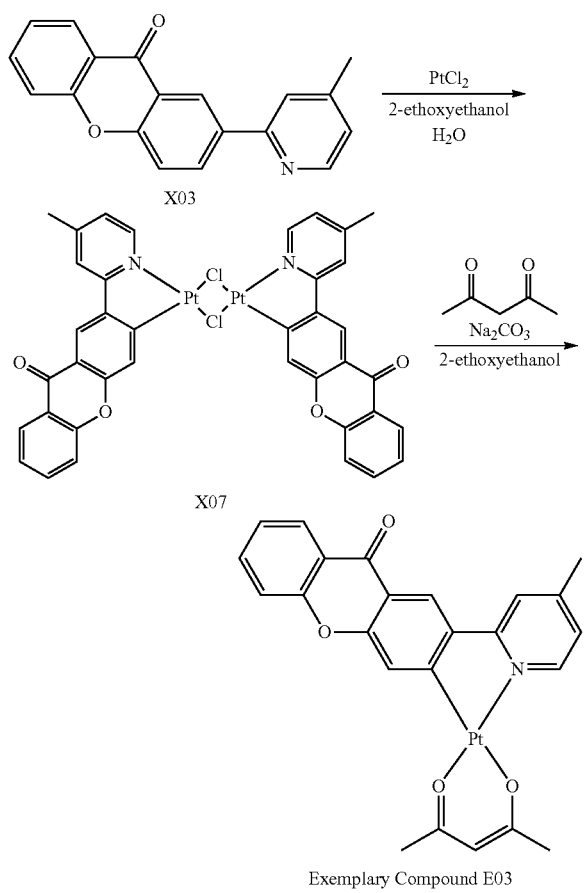

Exemplary Compound E03

(1) Synthesis of Intermediate Compound X07

The following reagents and solvents were loaded into a reaction vessel.

Platinum(II) chloride: 500 mg (1.88 mmol)
Intermediate compound X03: 513 mg (1.79 mmol)
2-Ethoxyethanol: 15 ml
Water: 5 ml Next, the reaction solution was heated under a nitrogen atmosphere to 100° C. and then stirred at the temperature (100° C.) for 12 hours. Next, the temperature of the reaction solution was returned to room temperature and then the precipitated solid was recovered by filtration. Next, the recovered residue was subjected to dispersion washing with 30 ml of methanol twice. Thus, 530 mg (0.512 mmol) of an intermediate compound X07 was obtained (54.5% yield). The resultant compound was confirmed to be the target product because a peak corresponding to a ratio m/z of 1,032 was observed by matrix-assisted laser desorption time-of-flight mass spectrometry (MALDI-TOF MS).

(2) Synthesis of Exemplary Compound E03

The following reagents and solvent were loaded into a reaction vessel.

Intermediate compound X07: 500 mg (0.484 mmol)
Acetylacetone: 484 mg (4.84 mmol)
Sodium carbonate: 513 mg (4.84 mmol)
2-Ethoxyethanol: 20 ml Next, the reaction solution was heated under a nitrogen atmosphere to 100° C. and then stirred at the temperature (100° C.) for 8 hours. Next, the temperature of the reaction solution was returned to room temperature and then the precipitated solid was recovered by filtration. Next, the recovered residue was subjected to dispersion washing with 20 ml of methanol twice. Next, the solid precipitated at the time of the performance of recrystallization with toluene was recovered. Thus, 464 mg (0.799 mmol) of an exemplary compound E03 was obtained (82.5% yield). The resultant compound was confirmed to be the target product because a peak corresponding to a ratio m/z of 580 was observed by matrix-assisted laser desorption time-of-flight mass spectrometry (MALDI-TOF MS).

In addition, 400 mg of the resultant exemplary compound E03 was subjected to sublimation purification with a sublimation purification system manufactured by ULVAC KIKO, Inc. It should be noted that during the sublimation purification, the degree of vacuum was set to $7.0 \times 10^{-1}$ Pa, the flow rate of an argon gas was set to 10 ml/min, and the sublimation temperature was set to 310° C. 321 milligrams of the exemplary compound E03 was obtained by the sublimation purification.

Meanwhile, the exemplary compound E03 obtained after the sublimation purification was confirmed to have a purity of 99.9% or more at a 254 nm absorption by high-performance liquid chromatography (HPLC) measurement.

On the other hand, a toluene solution of the exemplary compound E03 (concentration: $1 \times 10^{-5}$ mol/L) was prepared and then the emission spectrum of the toluene solution at an excitation wavelength of 300 nm was measured with an F-4500 manufactured by Hitachi, Ltd. As a result, its maximum emission wavelength was 469 nm. In addition, the quantum yield of the toluene solution measured with an absolute quantum yield meter (C9920-02 manufactured by Hamamatsu Photonics K.K.) was 0.05.

Further, thermal analysis measurement with a thermogravimetric/differential thermal analyzer (TG-DTA2000SA manufactured by Bruker) confirmed that no thermal decomposition occurred at 310° C.

Example 6

Synthesis of Exemplary Compound F03

An exemplary compound F03 was synthesized by the same method as that of Example 5 except that the compound X05 was used instead of the intermediate compound X03 in '(1)' of Example 5. In addition, the luminescence properties of the exemplary compound F03 were measured by the same method as that of Example 5. As a result, the maximum emission wavelength was 461 nm and the quantum yield was 0.03.

Example 7

Synthesis of Exemplary Compound E08

An exemplary compound E08 was synthesized by the same method as that of Example 5 except that the compound X06 was used instead of the intermediate compound X03 in '(1)' of Example 5. In addition, the luminescence properties of the exemplary compound E08 were measured by the same method as that of Example 5. As a result, the maximum emission wavelength was 470 nm and the quantum yield was 0.11.

Example 8

Production of Organic Electroluminescence Device

An organic electroluminescence device obtained by laminating an anode, a hole injection layer, a hole transporting layer, a luminescent layer, an electron transporting layer, and a cathode in the stated order was produced by the following method. Here, part of the compounds used in this example are shown below.

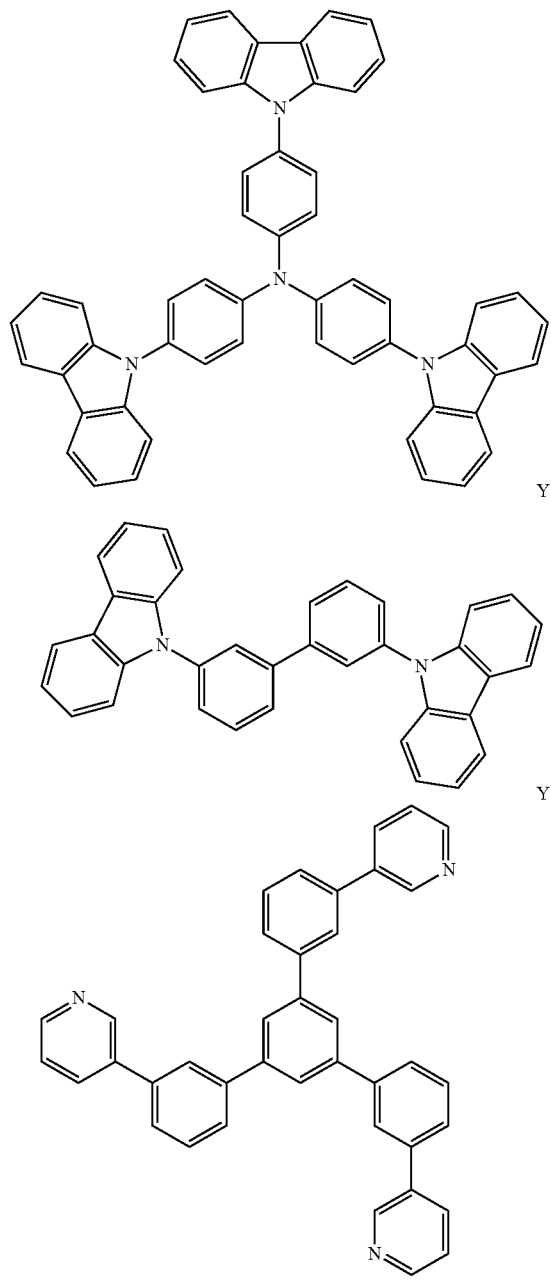

First, indium tin oxide (ITO) was formed into a film on a glass substrate by a sputtering method. Thus, the anode was formed. At this time, the thickness of the anode was set to 120 nm. Next, the substrate was sequentially subjected to ultrasonic washing with acetone and isopropyl alcohol (IPA), and was then subjected to boil washing with IPA, followed by drying. Further, the dried product was subjected to UV/ozone washing. The substrate with the anode treated by the foregoing method was used as a transparent conductive supporting substrate in the following steps.

Next, a chloroform solution was prepared by mixing the compound Y01 and chloroform. Next, the chloroform solution was dropped onto the transparent conductive supporting substrate and then a thin film to serve as a hole injection layer was formed by a spin coating method. At this time, the thickness of the hole injection layer was 30 nm.

Next, the substrate on which the hole injection layer had been formed was moved into a vacuum chamber, and then organic compound layers and electrode layers shown in Table 5 below were continuously formed by employing a vacuum vapor deposition method based on resistance heating. Thus, the organic electroluminescence device was produced. It should be noted that during the performance of the continuous formation, the pressure in the chamber was set to $1 \times 10^{-5}$ Pa.

TABLE 5

| Material | | Thickness [nm] |
|---|---|---|
| Hole transporting layer | Compound Y01 | 20 |
| Luminescent layer | Compound Y02 (host) Exemplary compound C01 (guest) (host:guest = 10:90 (weight ratio)) | 40 |
| Electron transporting layer | Compound Y03 | 30 |
| First metal electrode layer (cathode) | LiF | 0.5 |
| Second metal electrode layer (cathode) | Al | 150 |

The properties of the resultant organic electroluminescence device were measured and evaluated. Specifically, the current-voltage characteristics of the device were measured and evaluated with a microammeter 4140B manufactured by Hewlett-Packard Company, and the emission luminance of the organic electroluminescence device was measured and evaluated with a BM7 manufactured by TOPCON CORPORATION.

Here, at an emission luminance of 1,000 cd/m², the organic electroluminescence device of this example showed blue luminescence having coordinates (x, y) in a CIE standard colorimetric system of (0.16, 0.36), and showed high luminous efficiency, specifically, an external quantum yield of 9.1%. In addition, when a voltage was continuously applied to the organic electroluminescence device of this example under a nitrogen atmosphere for 100 hours, the device was observed to continuously show good luminescence.

Example 9

An organic electroluminescence device was produced by the same method as that of Example 8 except that the exemplary compound D01 was used instead of the exemplary compound C01 as a dopant in a luminescent layer in Example 8. The properties of the resultant organic electroluminescence device were measured and evaluated in the same manner as in Example 8. As a result, at an emission luminance of 1,000 cd/m², the device showed blue luminescence having coordinates (x, y) in a CIE standard colorimetric system of (0.15, 0.28), and showed high luminous efficiency, specifically, an external quantum yield of 8.2%. In addition, when a voltage was continuously applied to the organic electroluminescence device of this example under a nitrogen atmosphere for 100 hours, the device was observed to continuously show good luminescence.

Example 10

An organic electroluminescence device was produced by the same method as that of Example 8 except that the exemplary compound E03 was used instead of the exemplary compound C01 as a dopant in a luminescent layer in Example 8. The properties of the resultant organic electroluminescence device were measured and evaluated in the same manner as in Example 8. As a result, at an emission luminance of 1,000 cd/m², the device showed bluish green luminescence having coordinates (x, y) in a CIE standard colorimetric system of (0.16, 0.37), and showed high luminous efficiency, specifically, an external quantum yield of 9.9%. In addition, when a voltage was continuously applied to the organic electroluminescence device of this example under a nitrogen atmosphere for 100 hours, the device was observed to continuously show good luminescence.

As described above by listing the embodiment and the examples, the organic metal complex of the present invention is a compound that has a high quantum yield and emits light suitable for a blue color. Accordingly, when the complex is used as a constituent material for an organic electroluminescence device, an electroluminescence device having good luminescence properties can be obtained.

In addition, as described by indicating the embodiment and the examples, according to the present invention, there can be provided an organic electroluminescence device that emits blue light and is excellent in luminescence properties (in particular, external quantum yield).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-168943, filed Aug. 2, 2011, which is hereby incorporated by reference herein in its entirety.

The invention claimed is:

1. An organic metal complex, which is represented by the following general formula (1):

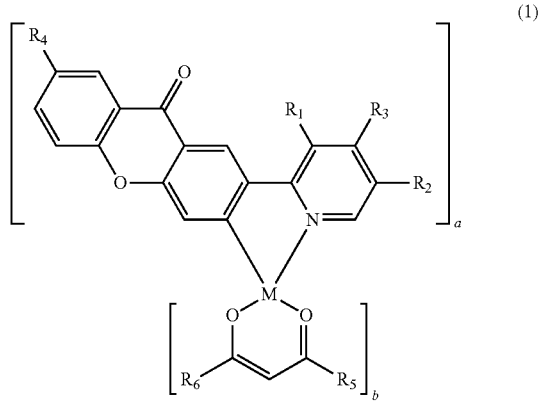

(1)

wherein in the formula (1), $R_1$ and $R_2$ each represent a hydrogen atom or an alkyl group having 1 to 4 carbon atoms, $R_3$ represents a hydrogen atom, an alkyl group having 1 to 4 carbon atoms, an alkoxy group having 1 to 6 carbon atoms, or an aryloxy group, $R_4$ represents a hydrogen atom or an alkyl group having 1 to 4 carbon atoms, $R_5$ and $R_6$ each represent an alkyl group having 1 to 4 carbon atoms, M represents Ir or Pt, and a and b each represent an integer, provided that:

when M represents Ir, the following requirements (A1) and (A2) are satisfied for a and b: (A1) a+b=3; and (A2) a represents 2 or 3; and when M represents Pt, the following requirements (B1) and (B2) are satisfied for a and b: (B1) a+b=2; and (B2) a represents 1 or 2.

2. The organic metal complex according to claim 1, wherein $R_1$, $R_2$, and $R_4$ each represent a hydrogen atom.

3. The organic metal complex according to claim 1, wherein $R_3$ represents a hydrogen atom or an alkyl group having 1 to 4 carbon atoms.

4. An organic electroluminescence device comprising:

a pair of electrodes; and an organic compound layer that is arranged between the pair of electrodes and has at least a luminescent layer, wherein the organic metal complex according to claim 1 is incorporated into the organic compound layer.

5. The organic electroluminescence device according to claim 4, wherein the luminescent layer comprises a host and a guest; and wherein the guest comprises the organic metal complex.

6. A display device comprising multiple pixels, wherein the pixels each comprise the organic electroluminescence device according to claim 4 and a switching element connected to the organic electroluminescence device.

7. An image input device comprising:

a display unit for displaying an image; and an input unit for inputting image information, wherein the display unit comprises multiple pixels; and wherein the pixels each comprise the organic electroluminescence device according to claim 4 and a switching element connected to the organic electroluminescence device.

8. An illumination device comprising:

the organic electroluminescence device according to claim 4; and an inverter circuit connected to the organic electroluminescence device.

* * * * *